(12) United States Patent
ElSohly et al.

(10) Patent No.: US 10,709,681 B2
(45) Date of Patent: Jul. 14, 2020

(54) BIOLOGICALLY ACTIVE CANNABIDIOL ANALOGS

(71) Applicant: University of Mississippi, University, MO (US)

(72) Inventors: Mahmoud A. ElSohly, Oxford, MS (US); Soumyajit Majumdar, Oxford, MS (US); Waseem Gul, Oxford, MS (US); Mohammad Khalid Ashfaq, Oxford, MS (US); Kenneth Joseph Sufka, Oxford, MS (US); Hannah Marie Harris, Kiln, MS (US)

(73) Assignee: UNIVERSITY OF MISSISSIPPI, University, MS (US)

( * ) Notice: Subject to any disclaimer, the term of this patent is extended or adjusted under 35 U.S.C. 154(b) by 0 days.

(21) Appl. No.: 16/073,766

(22) PCT Filed: Jan. 27, 2017

(86) PCT No.: PCT/US2017/015366
§ 371 (c)(1),
(2) Date: Jul. 27, 2018

(87) PCT Pub. No.: WO2017/132526
PCT Pub. Date: Aug. 3, 2017

(65) Prior Publication Data
US 2019/0031601 A1 Jan. 31, 2019

Related U.S. Application Data

(60) Provisional application No. 62/289,184, filed on Jan. 29, 2016.

(51) Int. Cl.
*A61K 31/24* (2006.01)
*A61K 31/225* (2006.01)
(Continued)

(52) U.S. Cl.
CPC ............. *A61K 31/24* (2013.01); *A61K 31/05* (2013.01); *A61K 31/223* (2013.01);
(Continued)

(58) Field of Classification Search
CPC .... A61K 31/27; A61K 31/235; A61K 31/265; A61K 31/24
(Continued)

(56) References Cited

U.S. PATENT DOCUMENTS 3,728,360 A 4/1973 Pars et al.
2009/0036523 A1* 2/2009 Stinchcomb ............ C07C 39/23
514/483
(Continued)

FOREIGN PATENT DOCUMENTS

WO WO 2008/107879 A1 9/2008
WO WO 2009/018389 A1 2/2009
(Continued)

OTHER PUBLICATIONS

Anderson, Chem & Biol (2003), vol. 10, pp. 787-797. (Year: 2003).*
(Continued)

*Primary Examiner* — Craig D Ricci
*Assistant Examiner* — Janet L. Coppins
(74) *Attorney, Agent, or Firm* — Hershkovitz & Associates, PLLC; Abe Hershkovitz; Eugene C. Rzucidlo

(57) ABSTRACT

Biologically active cannabidiol analogs comprising a compound of the formula
(Continued)

CBD plasma concentration (ng/mL) vs. time following rectal administration of two doses of CBD-Val-HS in a lipophilic base (Wecobee W) suppository formulation.

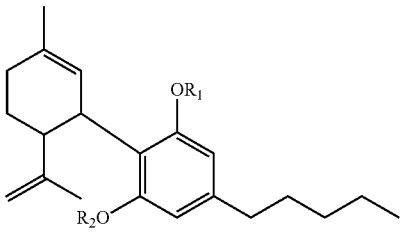

wherein one of $R_1$ or $R_2$ or both is/are the residue of a moiety formed by the reaction of an amino group of the amino acid ester of $R_1$ or $R_2$ or both with a dicarboxylic acid or a dicarboxylic acid derivative and the other $R_1$ or $R_2$ (in the case of the mono) is the residue of a dicarboxylic acid or dicarboxylic acid derivative or Hydrogen (H), (i.e. underivatized), and salts thereof. These CBD analogs are be useful in pain management in oncology and other clinical settings in which neuropathy is presented. Furthermore, these CBD-analogs are useful in blocking the addictive properties of opiates.

17 Claims, 14 Drawing Sheets

(51) Int. Cl.

| | |
|---|---|
| C07C 69/40 | (2006.01) |
| C07C 69/42 | (2006.01) |
| C07C 229/08 | (2006.01) |
| A61K 31/05 | (2006.01) |
| A61K 31/223 | (2006.01) |
| C07C 233/56 | (2006.01) |
| C07C 69/017 | (2006.01) |
| C07C 229/24 | (2006.01) |
| C07C 233/47 | (2006.01) |
| C07C 237/06 | (2006.01) |

(52) U.S. Cl.
CPC .......... *A61K 31/225* (2013.01); *C07C 69/017* (2013.01); *C07C 69/40* (2013.01); *C07C 69/42* (2013.01); *C07C 229/08* (2013.01); *C07C 229/24* (2013.01); *C07C 233/47* (2013.01); *C07C 233/56* (2013.01); *C07C 237/06* (2013.01); *C07C 2601/16* (2017.05)

(58) Field of Classification Search
USPC ...................................................... 514/483
See application file for complete search history.

(56) References Cited

U.S. PATENT DOCUMENTS

| | | |
|---|---|---|
| 2015/0045282 A1 | 2/2015 | ElSohly et al. |
| 2015/0218121 A1 | 8/2015 | Stinchcomb et al. |

FOREIGN PATENT DOCUMENTS

| | | |
|---|---|---|
| WO | WO 2010/051541 A2 | 5/2010 |
| WO | WO 2011/026144 A1 | 3/2011 |
| WO | WO 2014/134127 A1 | 9/2014 |

OTHER PUBLICATIONS

Burnstein, Bioorganic & Med Chem (2015), vol. 23, pp. 1377-1385. (Year: 2015).*
Thiel, Nature Biotechnology (2004), vol. 22(5), pp. 513-519. (Year: 2004).*
A. Alexander et al., Cannabinoids in the treatment of cancer, Cancer Lett. (2009), doi:10.1016/j.canlet.2009.04.005.
Amptoulach S., Tsavaris N. Neurotoxicity caused by the treatment with platinum analogues. Chemotherapy Research and Practice. 2011; Article ID 843019.
Basbaum AI, Fields HL. Endogenous pain control systems: brain-stem spinal pathways and endorphin circuitry. Annual Review of Neuroscience. 1984; 7:309-338.
Chiou LC, Hu SS, Ho Y. Targeting the cannabinoid system for pain relief? Act Anaesthesiologica Taiwanica. 2013; 51:161-170.
Cox ML, Haller VL, Welch SP. Synergy between Δ9-tetrahydro-cannabinol and morphine in the arthritic rat. European Journal of Pharmacology. 2007; 567:125-130.
Guindon J., Lai Y., Takacs SM, Bradshaw HB, Hohmann AG. Alterations in endocannabionid tone following chemotherapy-induced peripheral neuropathy: effects of endocannabinoid deactivation inhibitors targeting fatty-acid amide hydrolase and monoacylglycerol lipase in comparison to reference analgesics following cisplatin treatment. Pharmacological Research. 2012; 67, 94-109.
Hall W., Christie M., Currow D. Cannabinoids and cancer: causation, remediation, and palliation. The Lancet. 2005; 6:35-42.
Khasabova IA, Khasabov S., Paz J., Rose C., Simone DA. Cannabinoid type-1 receptor reduces pain and neurotoxicity produced by chemotherapy. Neurobiology of Disease. 2012; 32, 7091-7101.
Kim JH, Dougherty PM, Abdi S. Basic science and clinical management of painful and non-painful chemotherapy-related neuropathy. Gynecologic Oncology. 2015; 136:453-459.
Mansour A., Khachaturian H., Lewis ME, Akil H, Watson SJ. Anatomy of CNS opioid receptors. Trends in Neuroscience. 1988; 11: 308-314.
Miltenburg NC, Booger W. Chemotherapy-induced neuropathy: a comprehensive survey. Cancer Treatment Reviews. 2014; 40:872-882.
Neelakantan H., Tallarida RJ, Reishcenbach ZW, Tuma RF, Ward SJ, Walker EA. Distinct interactions of cannabidiol and morphine in three nociceptive behavioral models in mice. Behavioural Pharmacology. 2015; 26:304-314.
Paice JA. Chronic treatment-related pain in cancer survivors. Pain. 2010; 152:84-89.
Park HJ, Stokes JA, Pirie E., Skahen J., Shtaerman Y., Yaksh TL. Persistent hyperalgesia in the cisplatin-treated mouse as defined by threshold measures, the conditioned place preference paradigm, and the changes in dorsal root ganglia activated transcription factor 3: the effects of gabapentin, ketorolac, and entanercept. Anesthesia and Analgesia. 2013; 116:224-231.
Pisanti S., Picardi P., D'Alessandro A., Laezza C., Bifulco M. The endocannabinoid signaling system in cancer. Trends in Pharmacological Sciences. 2013; 34, 273-282.
Toth C., Au S. A prospective identification of neuropathic pain in specific chronic polyneuropathy syndromes and response to pharmacological therapy. Pain. 2008; 138:657-666.
Vera G, Cabezos PA, Martin MI, Abalo R. Characterization of cannabinoid-induced relief of neuropathic pain in a rat model of cisplatin-induced neuropathy. Pharmacology, Biochemistry and Behavior. 2013; 105, 205-212.
Wilson-Poe AR, Pocius E, Herschbach M, Morgan MM. The periaqueductal gray contributes to bi-directional enhancement of antinociception between morphine and cannabinoids. Pharmacology, Biochemistry and Behavior. 2013; 103: 444-449.
Wolf S., Barton D., Kottschade L., Grothey A., Lopriniz C. Chemotherapy-induced peripheral neuropathy: prevention and treatment strategies. European Journal of Cancer. 2008; 44:1507-1515.
International Search Report in International Application No. PCT/US2017/015366, dated Apr. 12, 2017.
International Preliminary Report on Patentability in International Application No. PCT/US2017/015366, dated Aug. 9, 2018.
Examination Report No. 1 in the counterpart Australian Application No. 2017212651, dated Jan. 17, 2019.

(56) References Cited

OTHER PUBLICATIONS

First Examination Report in the counterpart New Zealand Application No. 745595, dated Feb. 20, 2019.

* cited by examiner

Figure 1. CBD plasma concentration (ng/mL) vs. time following rectal administration of two doses of CBD-Val-HS in a lipophilic base (Wecobee W) suppository formulation.
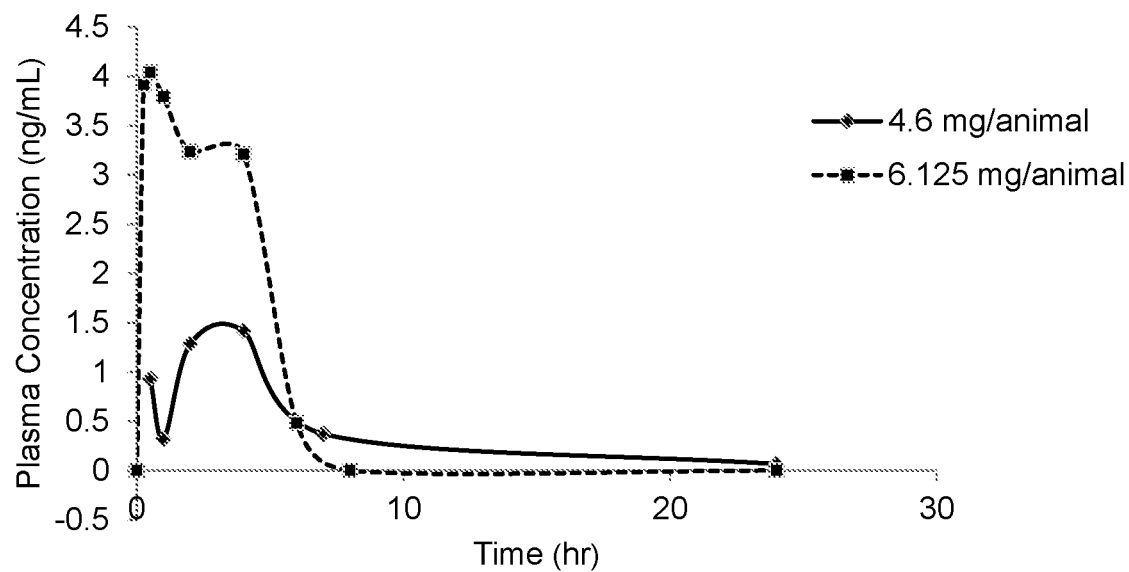
Figure 2. CBD concentration (ng/mL) vs time following rectal administration of 7 mg CBD-Val-HS in a hydrophilic base (PEG 1000) suppository formulation.
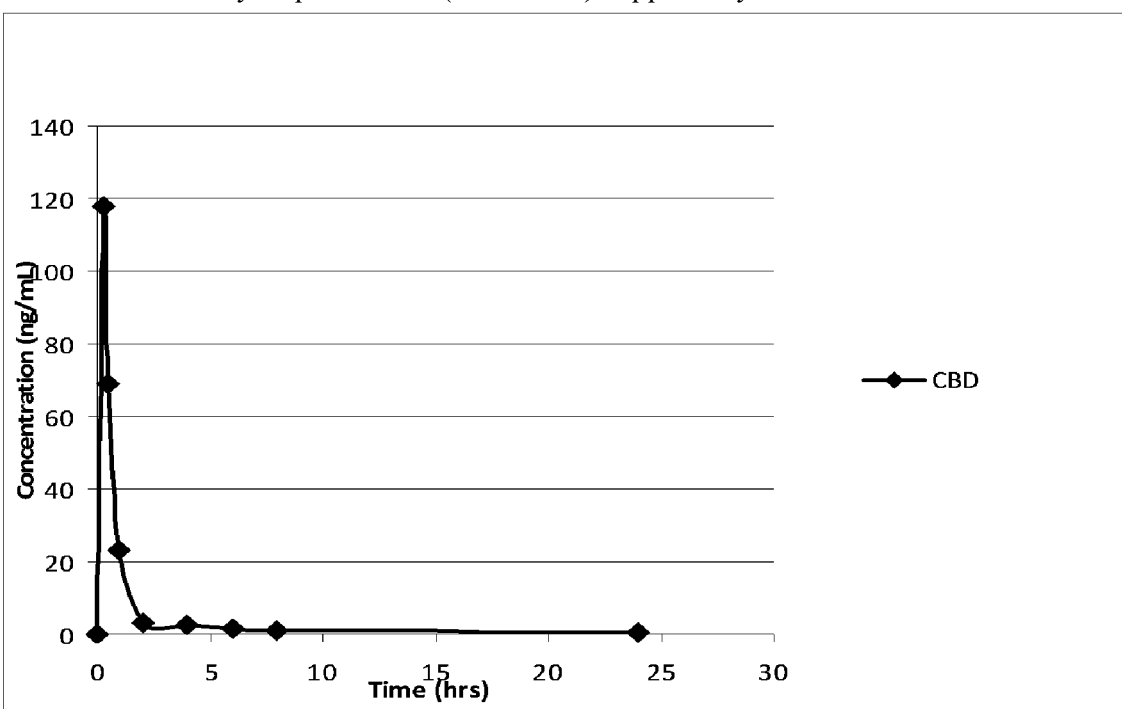

Figure 3. Plasma Concentration vs. Time Curve Post Administration of 7.5 mg of CBD-Mono-VHS in a Lipophilic (Wecobee M) Suppository Form in Rats
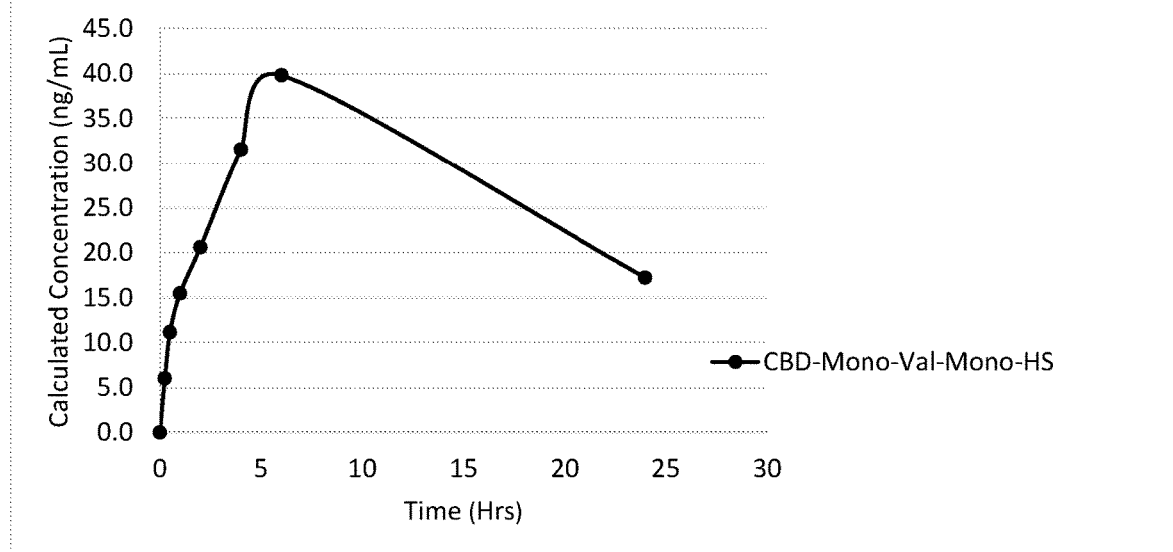
Figure 4. Plasma Concentration vs. Time Curve Post Administration of 7.5 mg of the CBD-Mono-VHS in a Hydrophilic (PEG 1000) Suppository Form in Rats
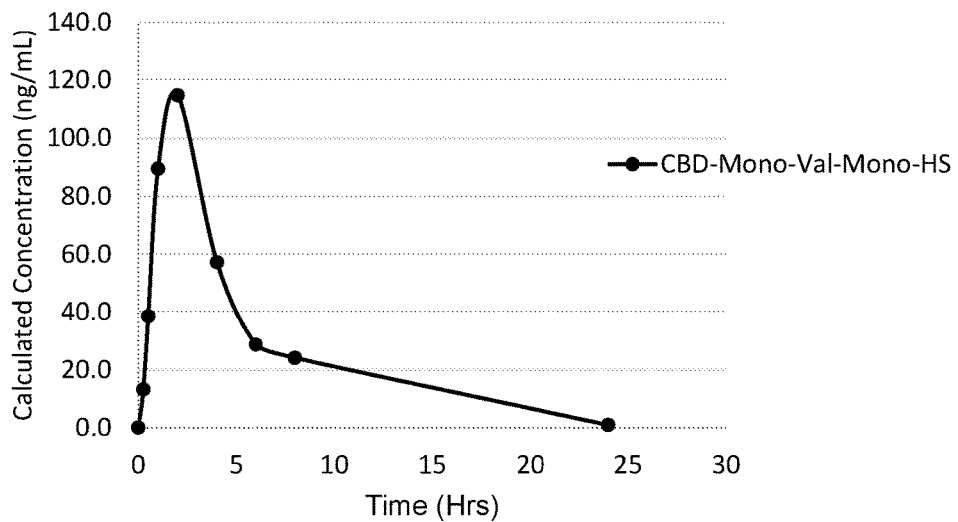

Figure 5. Plasma Concentration of CBD-Mono-VHS vs. Time Post Oral Administration of a 4 mg/animal Dose of the Drug
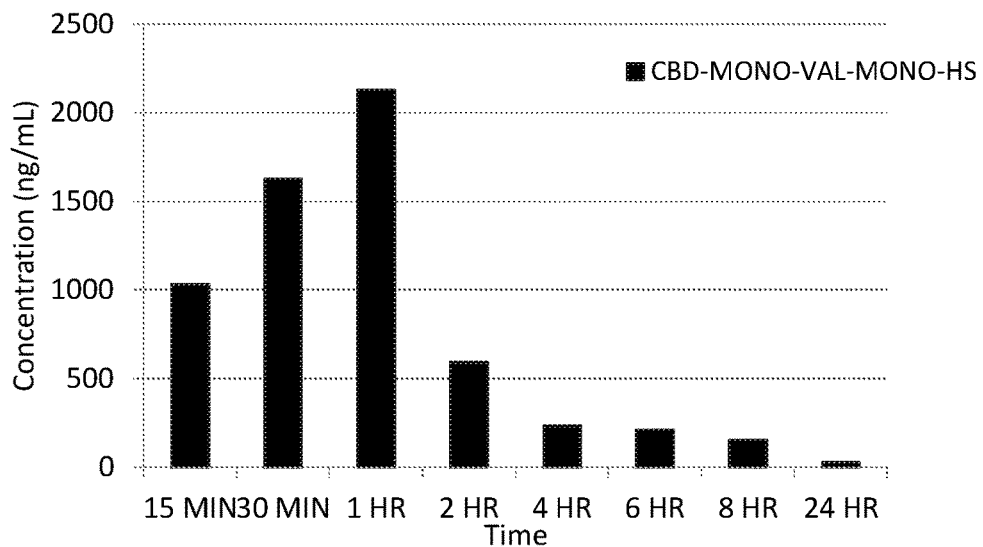
Figure 6a. CBD-Mono-Val-Mono-HS in different organs (liver, spleen, kidney, and brain) 2 and 4 Hr. post 4 mg oral dose of the drug
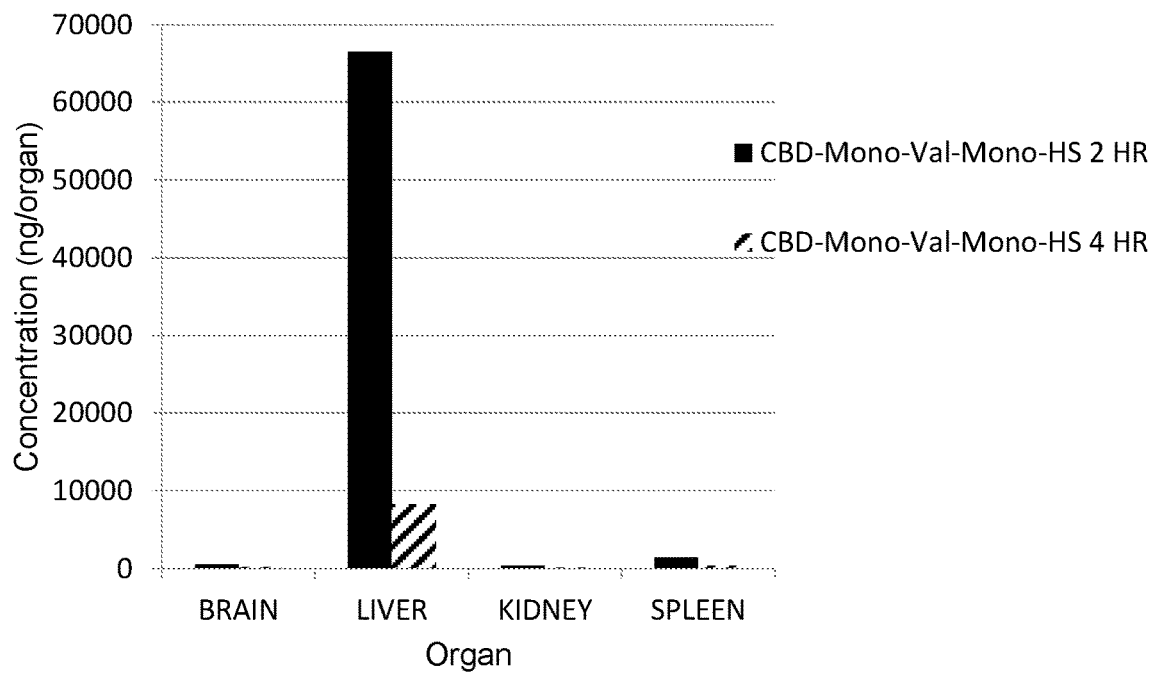

Figure 6b. CBD-Mono-Val-Mono-HS in Plasma 2 and 4 Hr. Post 4 mg Oral Dose of the Drug
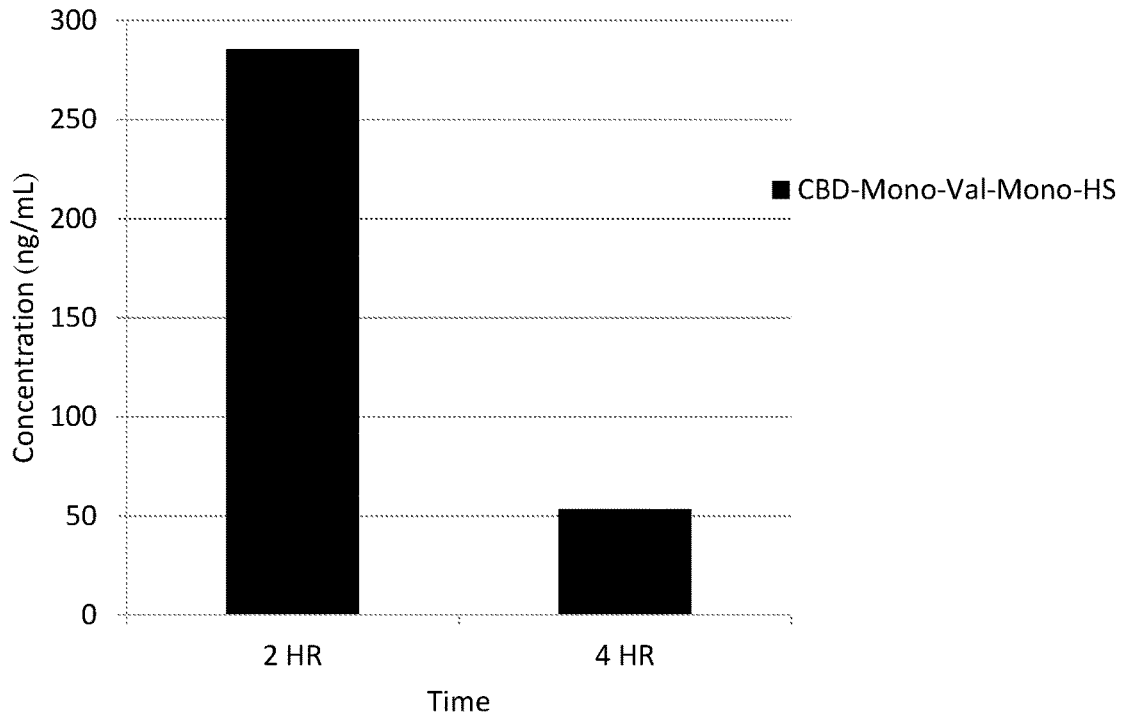
Figure 7a. Concentration of CBD and THC Post Incubation of CBD at pH 1.2 at different time intervals at 37°C
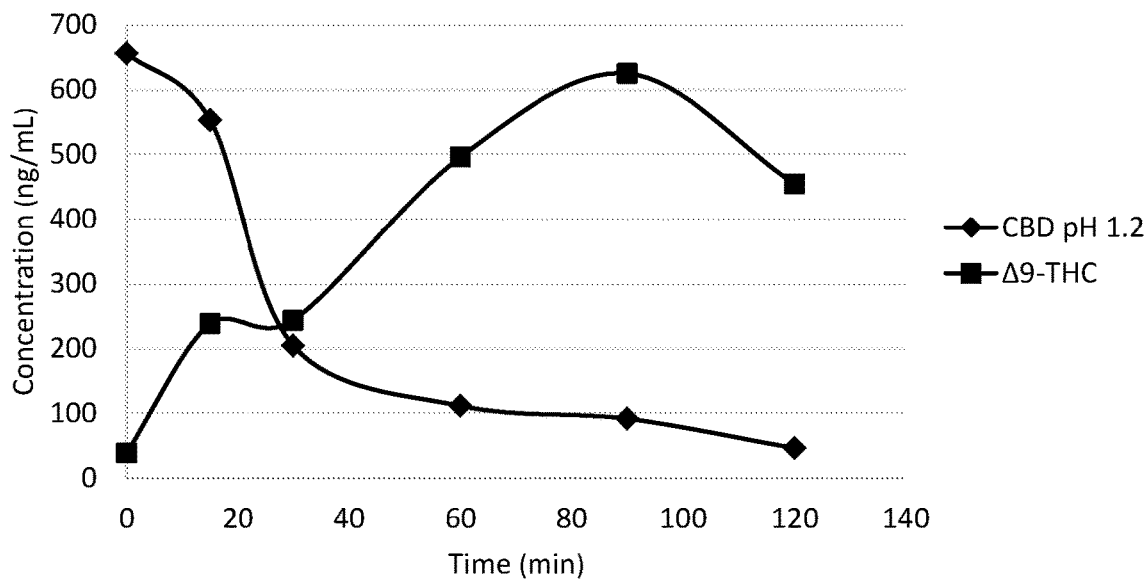

Figure 7b. Concentration of CBD After Incubation at pH 7.4 37°C at different time intervals (No THC was detected).
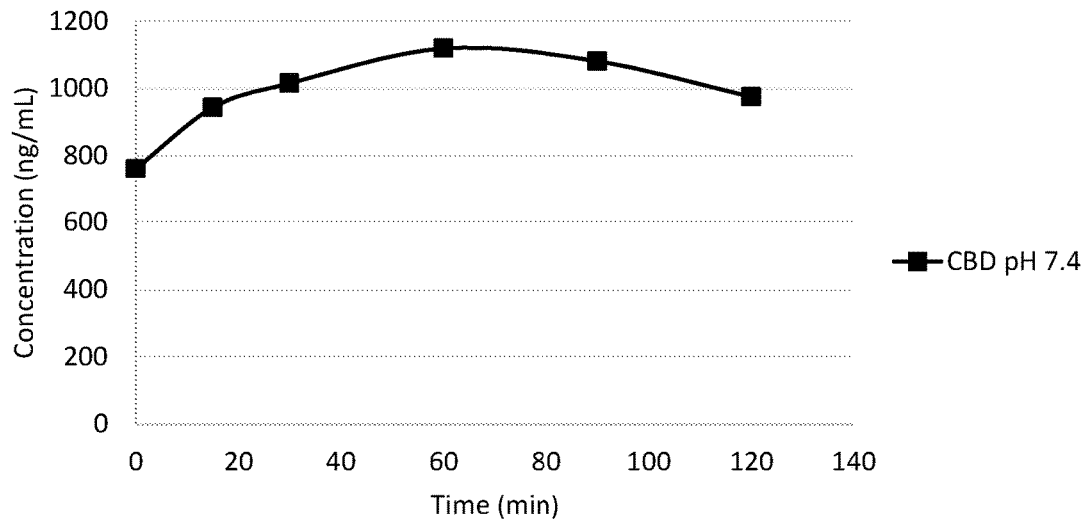
Figure 8. Concentration of CBD-Mono-Val-Mono-HS different pH's and time intervals
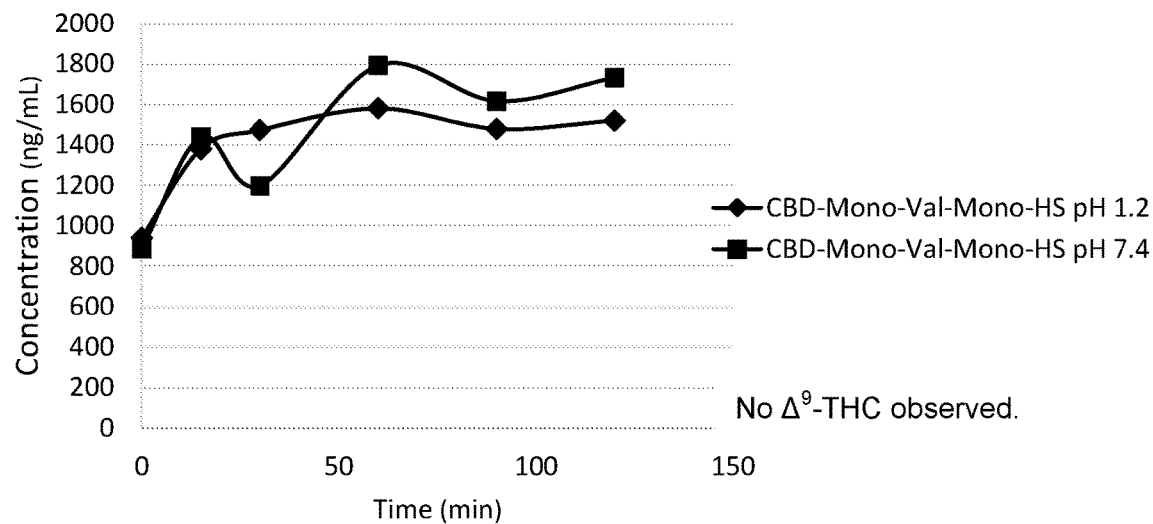

Figure 9. Concentration of CBD-Di-Val-Di-HS at different time intervals post incubation at pH 1.2 and 7.4
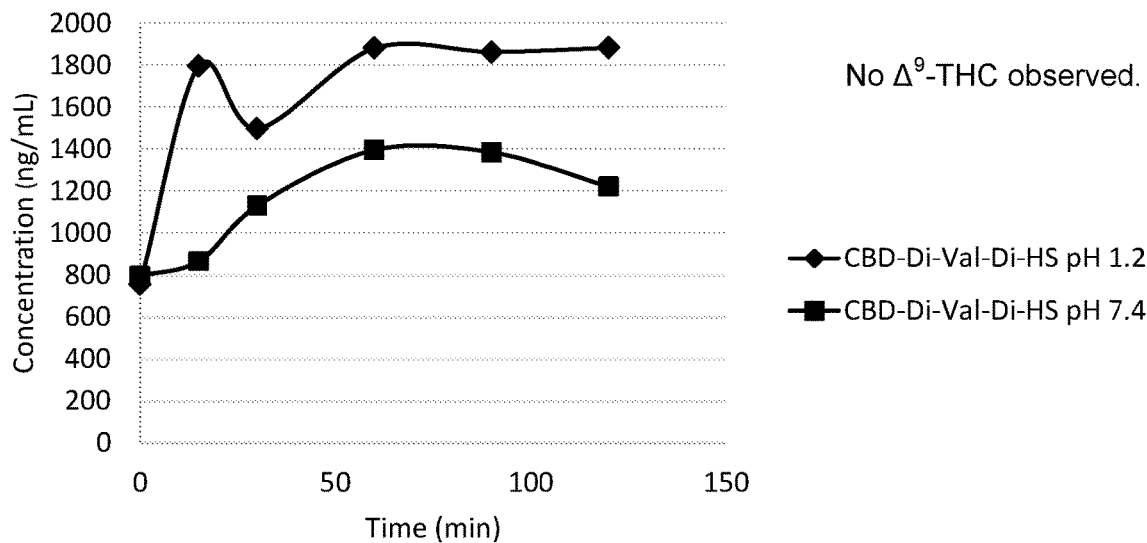
Figure 10. CBD Concentration in Plasma vs. Time Post Rectal Administration of 7.5 mg CBD-Hemiglutarate in a Lipophilic Suppository Formulation
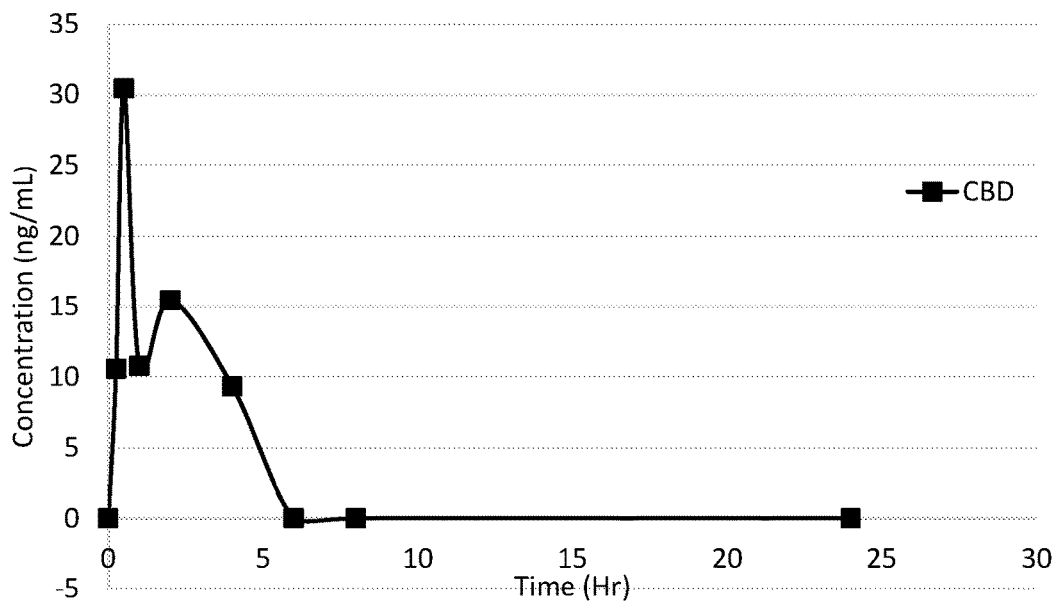

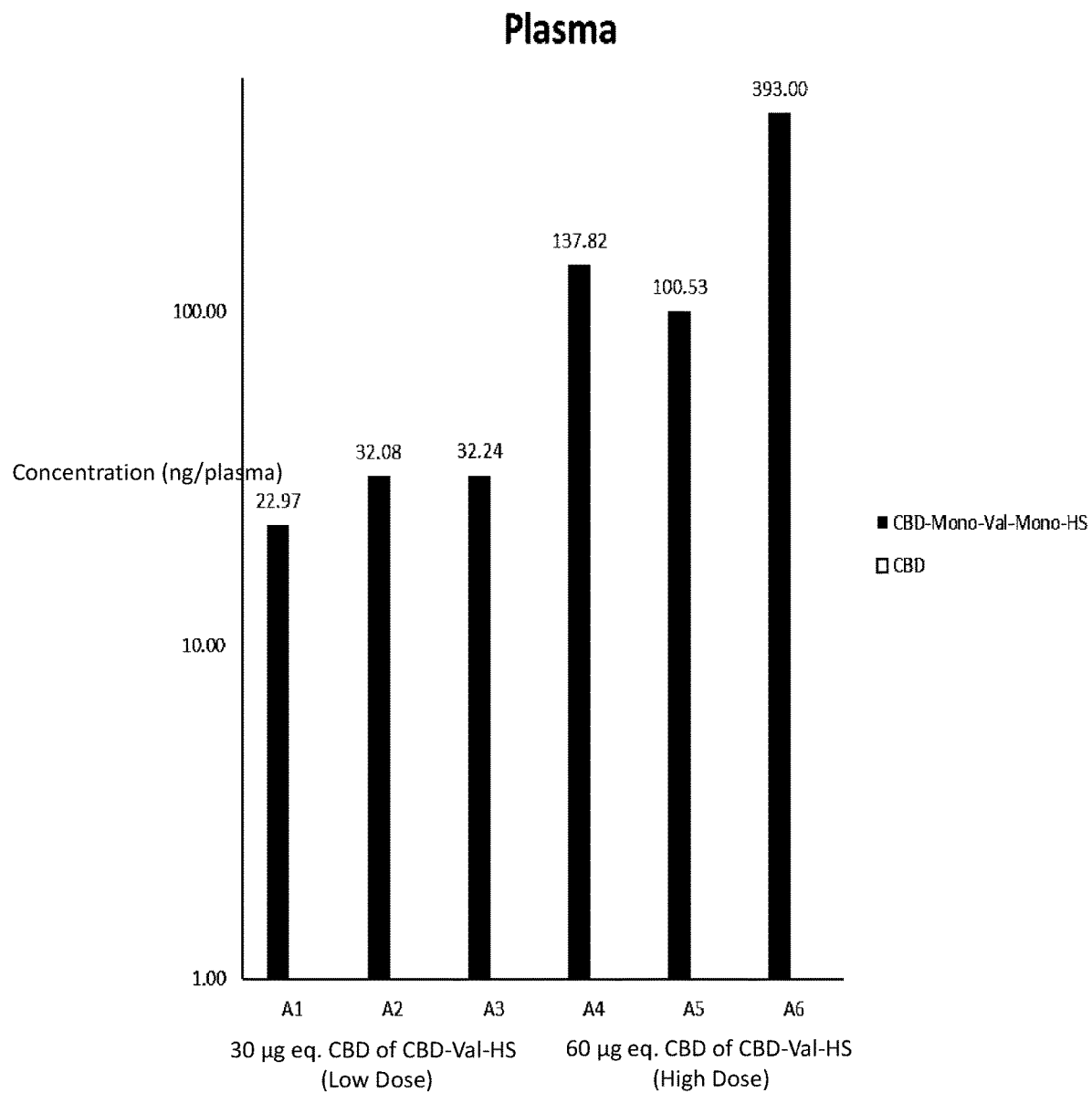
Figure 12. Plasma Concentration of CBD-Mono-VHS following IP Administration of the Dose Levels of the Drug 70 Minutes after Dosing

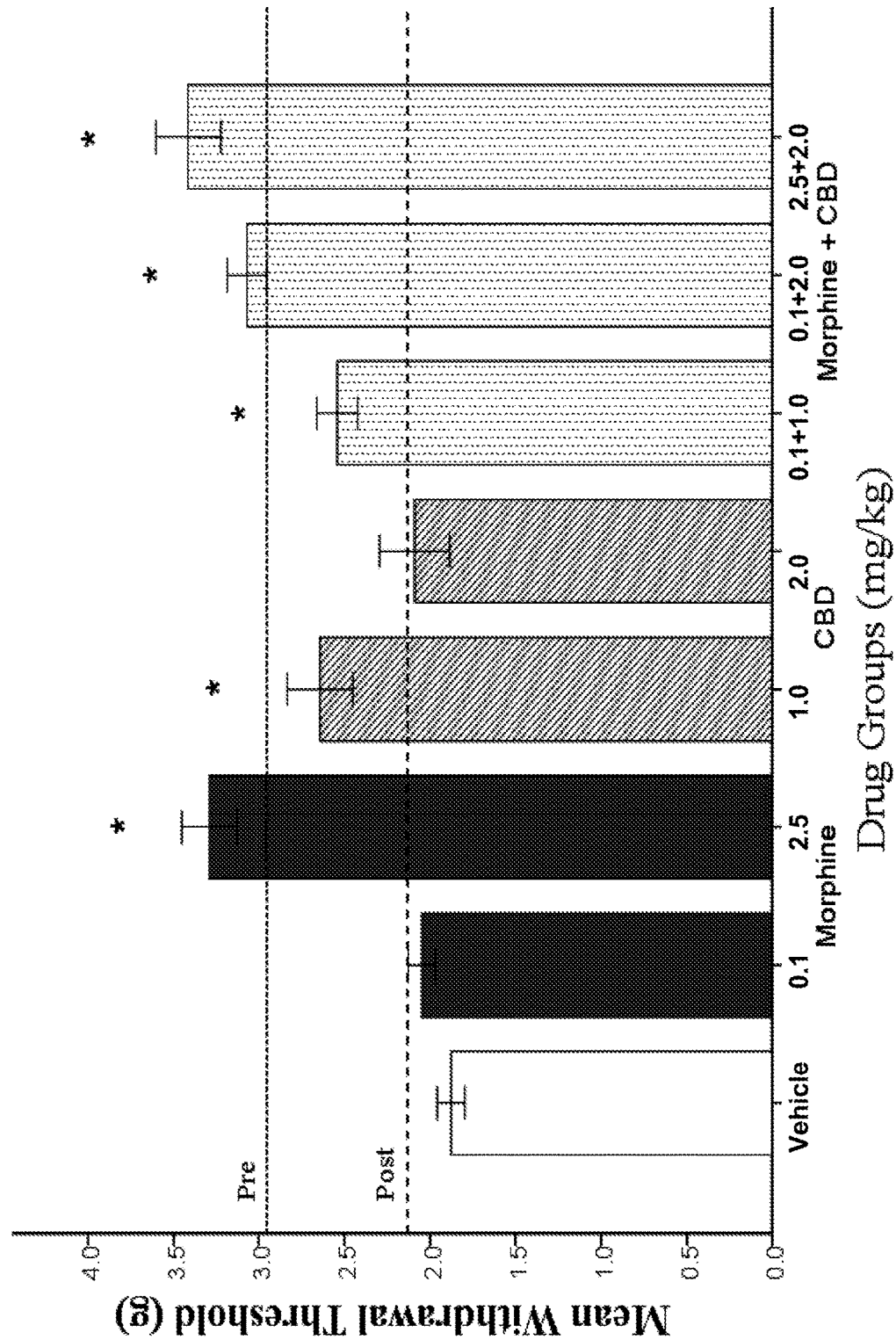

Figure 13. Mean paw withdrawal in grams of force (+/- SEM). Dashed lines depict baseline responses pre- and post-cisplatin administration protocol prior to drug efficacy screening. Vertical bars represent mean responses on drug (CBD-Val-HS) efficacy screening day. Doses are in mg/kg and delivered IP 45 minutes prior to testing. * denotes significant attenuation of tactile allodynia compared to the vehicle group (p < 0.05). Sample sizes were n = 5-14.

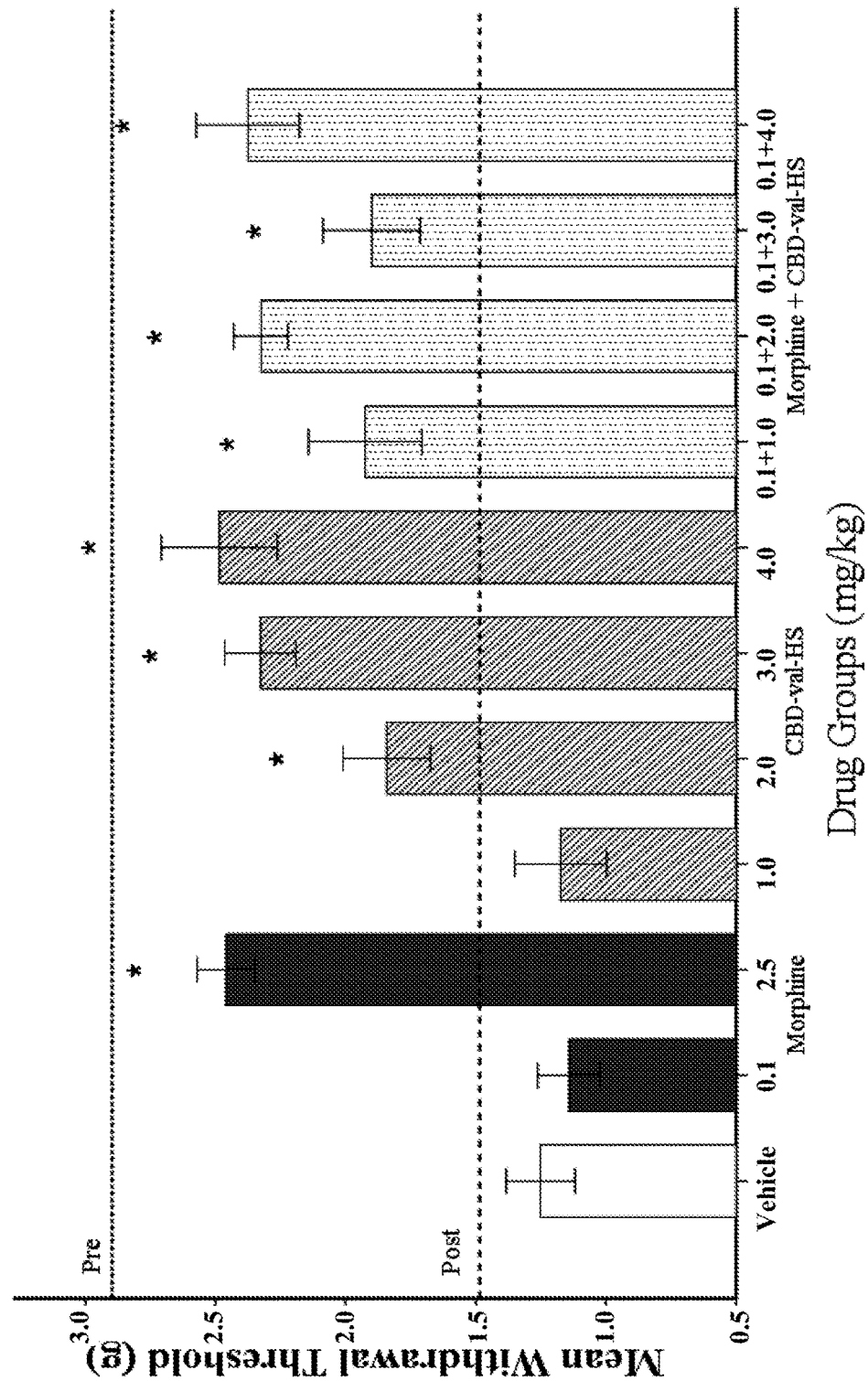

Figure 14. Mean paw withdrawal in grams of force (+/- SEM). Dashed lines depict baseline responses pre- and post-cisplatin administration protocol prior to drug efficacy screening. Vertical bars represent mean responses on drug (CBD-Val-HS) efficacy screening day. Doses are in mg/kg and delivered IP 45 minutes prior to testing. * denotes significant attenuation of tactile allodynia compared to the vehicle group ($p < 0.05$). Sample sizes were n = 9-11.

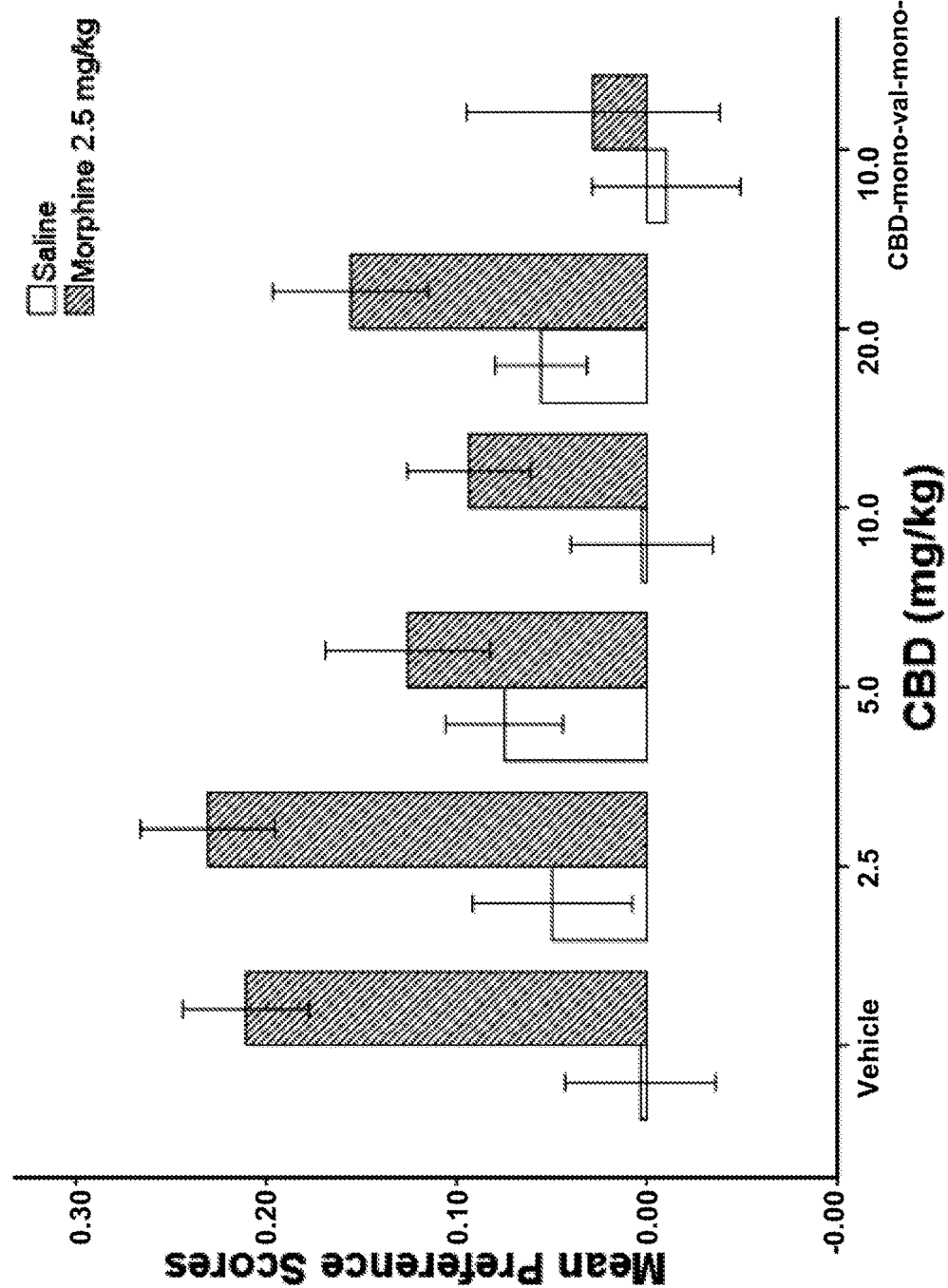

Figure 15. The effects of CBD and CBD-val-HS on morphine place preference scores. Values represent difference in the mean ratio of time (seconds) spent in the S+ (drug-paired) chamber during pre- and post-condition trials. Open bars reflect saline treated animals and striped bars represent morphine treated animals. *denotes significant difference form the vehicle group. † denotes significant attenuation of morphine preference. Sample sizes were n = 7-10.

BIOLOGICALLY ACTIVE CANNABIDIOL ANALOGS

FIELD OF THE INVENTION

The present invention is directed to the development of biologically active cannabidiol analogs capable of being formulated into pharmaceutical compositions, and methods of using such compositions for a pharmacological benefit. In a further embodiment of the present invention biologically active CBD analogs possessed analgesic properties alone and in combination of a sub-analgesic dose of morphine in cisplatin induced neuropathy. Furthermore, these analogs exhibited blocking properties to opiate addiction.

BACKGROUND OF THE INVENTION

Cannabidiol (CBD) has a variety of pharmacological benefits, including, but not limited to anti-inflammatory, analgesic, anti-convulsant, anti-psychotic, anti-fibrosis, anti-scarring, anti-oxidant, neuroprotective, anti-infective, anti-cancer and immunomodulatory effects.

Cisplatin is a common chemotherapy used to treat a variety of cancers. Unfortunately, cisplatin has a dose limiting effect wherein 50-85% of patients develop peripheral neuropathy 3-6 months into treatment. Cisplatin-induced neuropathy (CIN) presents in a "stocking and glove" distribution causing tingling paresthesia, numbness, and allodynia (Paice, 2010; Amptoulach et al., 2011). Pain management for CIN includes anticonvulsant, antidepressant, and non-steroidal anti-inflammatory drugs. These drugs prove to be well tolerated in patients but show little efficacy in treating CIN (Wolf et al., 2008; Amptoulach et al., 2011; Miltenburg et al., 2014).

While opioids can provide effective CIN pain relief, 76-96% of patients report aversive side effects that include sedation, nausea, and fatigue which limit usefulness and diminish patient quality of life (Guindon et al., 2008; Toth & Au, 2008). Added concerns of opioid therapy include tolerance, dose escalation, and dependence that can lead to withdrawal symptoms upon CIN resolution (Kim et al., 2015). Collectively, these observations suggest a need to develop novel pharmacotherapies for CIN.

Cannabinoids (CB) are used in oncology settings to control nausea, weight loss, lack of appetite, and chemotherapy related pain (Alexander et al., 2009). CB analgesia in both chronic and acute pain models is mediated through CB1 and CB2 receptors that are differentially expressed in the central and peripheral nervous systems (Chiou et al., 2013; Pisanti et al., 2013). An emerging body of literature supports the notion that CB systems may also modulate CIN. For example, CB1 and CB2 direct and indirect agonists attenuate tactile allodynia in rodent models of CIN (Vera et al., 2013; Guindon et al., 2012, Khasabova et al., 2012). However, like non-opioid therapies, CB compounds have modest efficacy and are of limited usefulness.

CB1 and opioid receptors are co-localized in pain pathways. Evidence suggest a dual pharmacotherapy at these targets may increase CB-mediated analgesic effects (Wilson-Poe et al., 2008; Hall et al., 2005; Mansour et al., 1988; Basbaum et al., 1984). For example, the CB1 agonist THC shows synergistic effects with sub-analgesic doses of the mu opioid agonist morphine in a rat arthritic pain model (Cox et al., 2007). However, use of any CB1 agonist in oncology settings is unlikely due to these compounds increasing the proliferation and growth of some tumor cells (Hall et al., 2005). Interestingly, other CB constituents that show low affinity to CB receptors also show synergistic effects with low dose opioids. For example, cannabidiol (CBD) shows synergistic effects with sub-analgesic doses of morphine in an acute pain model (i.e., acetic acid writhing) but not against thermal pain (Walker et al., 2015). Whether a combined CBD-opioid pharmacotherapy could provide highly efficacious pain relief against cisplatin neuropathy is unknown.

Challenges in pain management in oncology settings lead to unnecessary suffering, diminished quality of life, and in some instances, decreased life expectancy due to patients forgoing continued chemotherapy treatment. Current therapies against CIN are either only modestly effective or are fully effective but poorly tolerated.

SUMMARY OF THE INVENTION

Described herein are biologically active analogs of CBD that can be administered by a wide variety of routes of administration including but not limited to orally, transdermally or transmucosally (e.g. buccal, rectal, ocular, nasal) to a mammal, such as a human, for the treatment of a medical condition such as pain, inflammation, epilepsy and ocular diseases, including but not limited to treatment of diseases of the retina (e.g. diabetic retinopathy and macular degeneration).

It has been discovered that biologically active CBD analogs containing a natural amino acid and a dicarboxylic acid moiety attached to one of the hydroxyl groups (with the amino acid linked to CBD through an ester linkage and the dicarboxylic acid attached to the amino group of the amino acid in an amide linkage) with the other hydroxyl group free, result in higher than expected concentrations in vivo. Furthermore, the amino acid esters of CBD (di esters) must be reacted with a dicarboxylic acid, forming amide linkages with the free amine group of the cannabidiol-amino acid ester, to affect bioavailability in vivo. Exemplary CBD analogs can be represented by the following formulae:

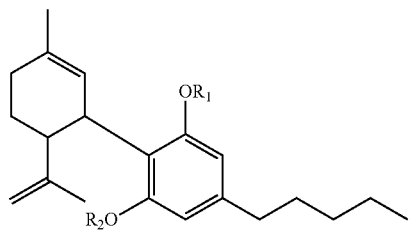

$R_1$ and $R_2 =$

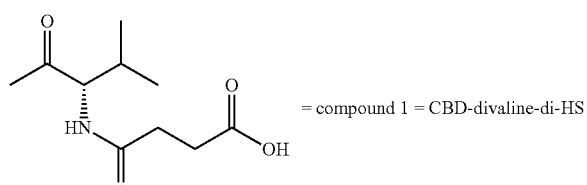

= compound 1 = CBD-divaline-di-HS $R_1$ OR $R_2 =$ 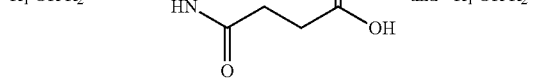 and $R_1$ OR $R_2 =$ -continued

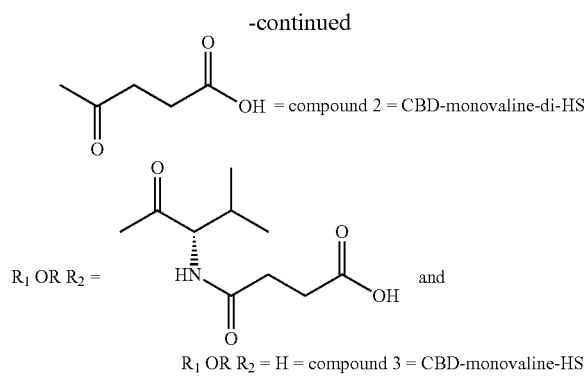

R₁ OR R₂ = H = compound 3 = CBD-monovaline-HS

The structures of CBD-divalinate-dihemisuccinate (1) CBD-mono-valinate-di-hemisuccinate (2) and CBD-monovalinate-hemisuccinate (3) are shown above.

In general, the analogs of the present invention can be represented by the following generic formula I:

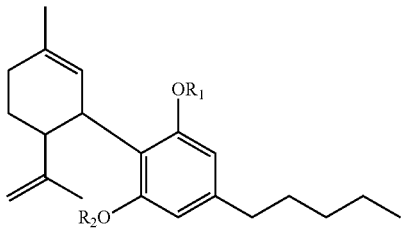

This formula I shows the structure for amino acid ester and/or dicarboxylic acid ester analogs wherein $R_1$ or $R_2$ or both is/are the residue of a moiety formed by the reaction of the amino group of the amino acid ester with a dicarboxylic acid or a dicarboxylic acid derivative and $R_1$ or $R_2$ (in case of the mono amino acid ester) is the residue of a dicarboxylic acid or dicarboxylic acid derivative or a Hydrogen (H). Both $R_1$ and $R_2$ could be residues of moieties formed by reaction of the amine group of the amino acid ester at both sites with a dicarboxylic acid.

The biologically active analogs of the invention can be formed from amino acids including, for example, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, homoserine lactone, and norleucine. By a "dicarboxylic acid" herein is meant an organic acid that has two carboxyl groups (—COOH). The general molecular formula for dicarboxylic acids can be written as $HO_2C$—R—$CO_2H$, where R can be straight chain or branched aliphatic or aromatic. Examples of suitable dicarboxylic acids in this invention include, but are not limited to, malonic acid, malic acid, glutaric acid, succinic acid, and phthalic acid. Dicarboxylic acids are reacted as their anhydrides and reactive derivatives of dicarboxylic acids such as, for example, dicarboxylic acid halides.

In a further embodiment of this invention, it has been found that biologically active CBD analogs such as described above including, for example CBD-val-HS, possess several attributes that suggest that biologically active CBD analogs may be useful in pain management. First, CBD-val-HS has much better absorption and a longer biological half-life than CBD. More importantly, CBD-val-HS is biologically active and fully efficacious as certain opioids in this CIN murine model. Collectively, these findings strongly argue that biologically active CBD analogs be considered in pain management in oncology and, perhaps, other clinical settings in which neuropathy is presented. Furthermore, these biologically active analogs of CBD were found to possess stronger activity than CBD itself in blocking the morphine additive properties.

This suggests that a combination of these CBD derivatives with morphine and/or other opiates would have better analgesic activity than morphine and/or other opiates used alone while also preventing addiction to morphine and/or other opiates cause by their extended use.

DETAILED DESCRIPTION OF THE INVENTION

The present invention comprises compounds of the formula I

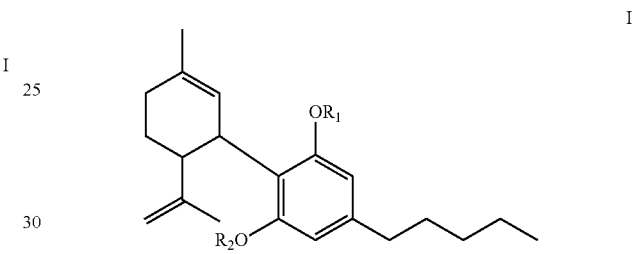

wherein one of $R_1$ or $R_2$ or both is/are the residue of a moiety formed by the reaction of an amino group of the amino acid ester of $R_1$ or $R_2$ or both with a dicarboxylic acid or a dicarboxylic acid derivative and the other $R_1$ or $R_2$ (in the case of the mono) is the residue of a dicarboxylic acid or dicarboxylic acid derivative or Hydrogen (H), (i.e. underivatized), and salts thereof.

The amino acid is can be, but not limited to the listed, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

The present invention still further comprises biologically active compounds of the formula II:

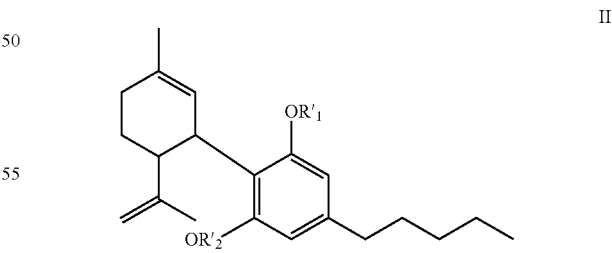

wherein $R'_1$ and $R'_2$ or both are ester residue(s) of natural amino acids and derivatives thereof and salts thereof.

The amino acid ester(s) is (are) selected from but not limited to one of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine and derivatives thereof and salts thereof.

The compounds of the present invention can be described as compounds of the formula III:

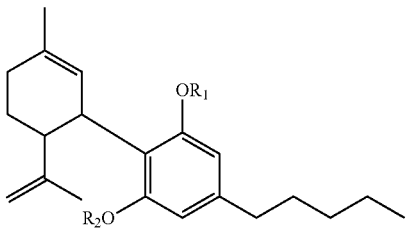

III wherein one of $R_1$ or $R_2$ or both is/are an amino acid ester residue of a moiety formed by the reaction of a carboxyl group of an amino acid with one or both phenolic groups of cannabidiol; or one of $R_1$ or $R_2$ or both is/are an ester residue of a moiety formed by the reaction of a carboxyl group of a dicarboxylic acid or dicarboxylic acid derivative with one or both phenolic groups of cannabidiol; or one of $R_1$ or $R_2$ is the amino acid ester residue of the reaction of the phenolic group of cannabidiol with the carboxyl group of an amino acid and the other $R_1$ or $R_2$ is the ester residue of the reaction of the phenolic group of cannabidiol with the carboxyl of a dicarboxylic acid or dicarboxylic acid derivative; or one of $R_1$ or $R_2$ (in the case of the mono) is hydrogen (H), (i.e. underivatized) and the other $R_1$ or $R_2$ is an amino acid ester residue or an ester residue, and salts thereof.

One or both $R_1$ and $R_2$ is/are an amino acid ester moiety which is further reacted with a dicarboxylic acid or dicarboxylic acid derivative to form an amide moiety by the reaction of the amino group of the amino acid ester with a carboxyl moiety of the dicarboxylic acid or dicarboxylic acid derivative.

The amino acid is any but not limited to one of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

In one embodiment of the present invention $R_1$ or $R_2$ or both are ester residue(s) of natural amino acids and derivatives thereof and salts thereof.

Exemplary but not exclusive examples of the present invention include: the compound is CBD-Di-Glutaminate, CBD-Di-Hemisuccinate, CBD-Di-Alaninate Ester, CBD-Di-Alaninate-Di-Hemisuccinate, CBD-Di-Valinate, CBD-Di-Valinate-Di-HS, CBD-Di-Hemiglutarate, CBD-Mono-Valinate, CBD-Mono-Valinate-Mono-Hemisuccinate, or CBD-monovalinate-dihemisuccinate.

The present invention further encompasses a formulation for administration of a biologically active CBD analog for the treatment of a disease condition comprising a therapeutically effective amount of at least one compound of formula I, II or III in an acceptable base or carrier.

Exemplary but not exclusive formulations according to the present invention are formulations such as: 1) a formulation which is a suppository formulation in an acceptable suppository base; 2) a formulation which is an oral formulation (e.g. tablet, capsule or liquid); 2) a formulation which is a transmucosal delivery formulation; 3) a formulation which is a topical ophthalmic formulation (e.g. a liquid, semi-solid or implant) for reducing the intraocular pressure and/or inflammation in the treatment of glaucoma and/or eye inflammation uveitis in an acceptable ophthalmic carrier; 4) an external or internal depot delivery system for the eye (e.g. a pump, bio-erodible device, or subcutaneous placed depot); 5) a topical formulation for application to the skin (e.g. a lotion, gel, or ointment). The topical ophthalmic formulations can be for example a formulation which is a polymeric ocular film using lipid Nano particles.

A further embodiment of the present invention is a formulation for administration of a biologically active CBD analog to a subject in need of treatment of a disease condition comprising a therapeutically effective amount of at least one compound of per formula I in an acceptable base or carrier.

The formulation for administration of a biologically active CBD analog to a subject in need of treatment of a disease condition comprising a therapeutically effective amount of at least one compound wherein the compound is CBD-Di-Glutaminate, CBD-Di-Hemisuccinate, CBD-Di-Alaninate Ester, CBD-Di-Alaninate-Di-Hemisuccinate, CBD-Di-Valinate, CBD-Di-Valinate-Di-HS, CBD-Di-Hemiglutarate, CBD-Mono-Valinate, CBD-Mono-Valinate-Mono-Hemisuccinate, or CBD-monovalinate-dihemisuccinate in an acceptable base or carrier.

The formulation can comprise a suppository formulation in an acceptable suppository base; an oral formulation; a transmucosal delivery formulation; a topical ophthalmic formulation; or an external or internal depot delivery system.

A still further embodiment of the present invention is a method of treating pain management comprising administering to a subject in need of such treatment an effective amount of at least one compound according formula I. The compound used in the present method is at least one compound wherein the compound is CBD-Di-Glutaminate, CBD-Di-Hemisuccinate, CBD-Di-Alaninate Ester, CBD-Di-Alaninate-Di-Hemisuccinate, CBD-Di-Valinate, CBD-Di-Valinate-Di-HS, CBD-Di-Hemiglutarate, CBD-Mono-Valinate, CBD-Mono-Valinate-Mono-Hemisuccinate, or CBD-monovalinate-dihemisuccinate in an acceptable base or carrier.

The pain management can be, for example, pain management in oncology or neuropathic pain management.

Additionally, the present invention relates to a method of blocking opiate additive properties and comprises administering to a subject in need of such treatment an effective amount of at least one compound per formula I. Preferably the compound used in this method is at least one compound wherein the compound is CBD-Di-Glutaminate, CBD-Di-Hemisuccinate, CBD-Di-Alaninate Ester, CBD-Di-Alaninate-Di-Hemisuccinate, CBD-Di-Valinate, CBD-Di-Valinate-Di-HS, CBD-Di-Hemiglutarate, CBD-Mono-Valinate, CBD-Mono-Valinate-Mono-Hemisuccinate, or CBD-monovalinate-dihemisuccinate in an acceptable base or carrier.

The present invention can also encompass a method of preventing addiction to morphine because of extended morphine use comprising administering to a subject in need of such treatment an effective amount of at least one compound per formula I or preferably the compound used in this method is at least one compound wherein the compound is CBD-Di-Glutaminate, CBD-Di-Hemisuccinate, CBD-Di-Alaninate Ester, CBD-Di-Alaninate-Di-Hemisuccinate, CBD-Di-Valinate, CBD-Di-Valinate-Di-HS, CBD-Di-Hemiglutarate, CBD-Mono-Valinate, CBD-Mono-Valinate-Mono-Hemisuccinate, or CBD-monovalinate-dihemisuccinate in an acceptable base or carrier.

BRIEF DESCRIPTION OF THE FIGURES

FIG. 1 shows plasma levels of CBD vs time following rectal administration of 6.125 mg or 4.625 mg CBD-Val-HS in a lipophilic suppository (Wecobe W base).

FIG. 2 shows the plasma levels of CBD following the rectal administration of 7 mg CBD-Val-HS in a hydrophilic base (PEG 1000).

FIG. 3 shows plasma levels of CBD-Mono-VHS vs. time following rectal administration of 7.5 mg CBD-Mono-VHS in a lipophilic suppository (Wecobe W base).

FIG. 4 shows plasma levels of CBD-Mono-VHS vs. time following rectal administration of 7.5 mg CBD-Mono-VHS in a hydrophilic suppository (PEG 1000 base).

FIG. 5 shows plasma levels of CBD-Mono-VHS vs. time following oral administration of 4 mg CBD-Mono-VHS in sesame seed oil.

FIG. 6a shows organ levels of CBD-Mono-VHS in 2 and 4 hr. post oral administration of 4 mg CBD-Mono-VHS.

FIG. 6b shows plasma levels of CBD-Mono-VHS in 2 and 4 hr. post oral administration of 4 mg CBD-Mono-VHS.

FIG. 7a shows concentration of CBD and THC vs. time post incubation of CBD at 37° C. at pH 1.2.

FIG. 7b shows concentration of CBD vs. time post incubation of CBD at 37° C. at pH 7.4.

FIG. 8 shows concentration of CBD-Mono-VHS vs. time at pH's of 1.2 and 7.4.

FIG. 9 shows concentration of CBD-Di-VHS post incubation at 37° C. vs. time at pHs of 1.2 and 7.4.

FIG. 10 shows plasma levels of CBD vs. time following rectal administration of 7.5 mg CBD-HG in a lipophilic suppository (Wecobe W base).

FIG. 12 shows plasma concentration of CBD-Mono-VHS 70 minutes after IP administration of two doses (30 and 60 µg) of CBD-Mono-VHS in mice.

FIG. 13 shows mean paw withdrawal in grams of force (+/−SEM). Dashed lines depict baseline responses pre- and post-cisplatin administration protocol prior to drug efficacy screening. Vertical bars represent mean responses on drug CBD-Val-HS efficacy screening day. Doses are in mg/kg and delivered IP 45 minutes prior to testing. * denotes significant attenuation of tactile allodynia compared to the vehicle group ($p<0.05$). Sample sizes were n=5-14.

FIG. 14 shows mean paw withdrawal in grams of force (+/−SEM). Dashed lines depict baseline responses pre- and post-cisplatin administration protocol prior to drug efficacy screening. Vertical bars represent mean responses on drug CBD-Val-HS efficacy screening day. Doses are in mg/kg and delivered IP 45 minutes prior to testing. * denotes significant attenuation of tactile allodynia compared to the vehicle group ($p<0.05$). Sample sizes were n=9-11.

FIG. 15 shows the effects of CBD and CBD-val-HS on morphine place preference scores. Values represent difference in the mean ratio of time (seconds) spent in the S+ (drug-paired) chamber during pre- and post-condition trials. Open bars reflect saline treated animals and striped bars represent morphine treated animals. *denotes significant difference form the vehicle group. † denotes significant attenuation of morphine preference. Sample sizes were n=7-10.

CBD-AMINO ACID ESTER SYNTHESIS

Example 1: Synthesis of CBD-Di-Glutaminate

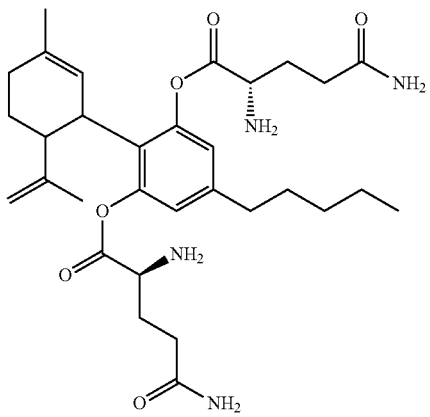

Figure 11A:
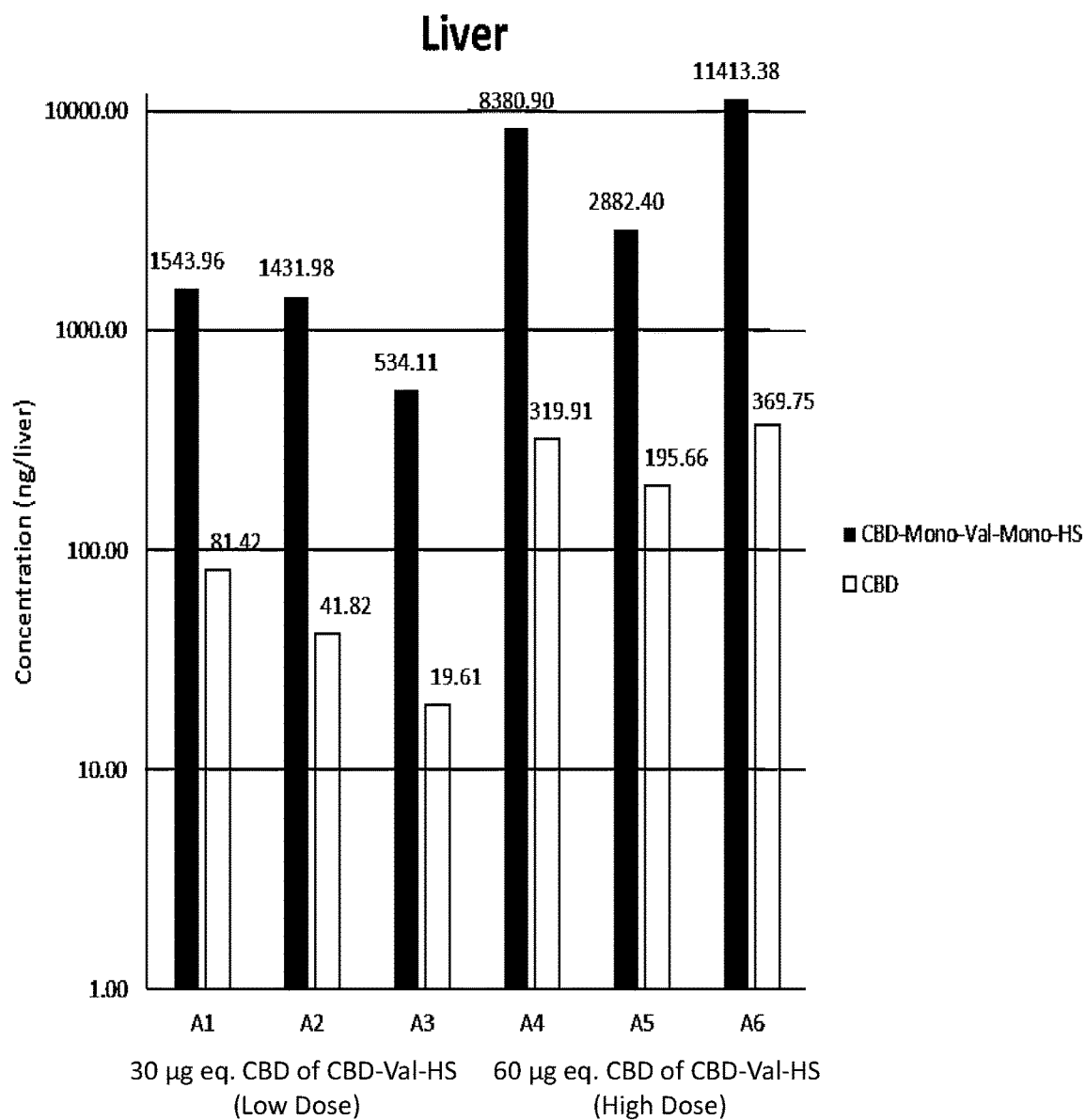
FIGS. 11a-d show organ levels of CBD and CBD-Mono-VHS 70 minutes after IP administration of two doses (30 and 60 µg) of CBD-Mono-VHS in mice: a) liver levels, b) spleen levels, c) kidney levels, and d) brain levels.

CBD-Di-Glutaminate
Chemical Formula: $C_{31}H_{46}N_4O_6$
Molecular Weight: 570.73

Structure of CBD-Di-Glutaminate (CBD-Di-Gln).

A. Synthesis of CBD-Diglutaminate-Boc (CBD-Di-Gln-Boc)

CBD was dissolved in DCM and catalytic amount of DMAP was added to it while stirring. Boc-glutamine (2.2 eq.) was dissolved in DCM and 2.2 eq. of DCC was added to it while stirring. CBD/DMAP solution was added to Boc-glutamine/DCC solution and allowed to stir for 30 minutes. Thin layer chromatography (10% EtOAc/90% Hexane) indicated the completion of reaction. The product was purified using silica gel and product was eluted (in 90% EtOAc/10% Hexane) as pure compound.

B. Deprotection of CBD-Di-Gln-Boc to CBD-Di-Gln

CBD-di-Gln-boc was dissolved in THF while stirring. $HCl_{(g)}$ was bubbled through it for approximately 3 minutes while stirring. Excess $HCl_{(g)}$ was removed with $N_{2(g)}$ and the solvent was evaporated. Product was confirmed by mass spectrometry.

Example 2: Synthesis of CBD-Di-Hemisuccinate

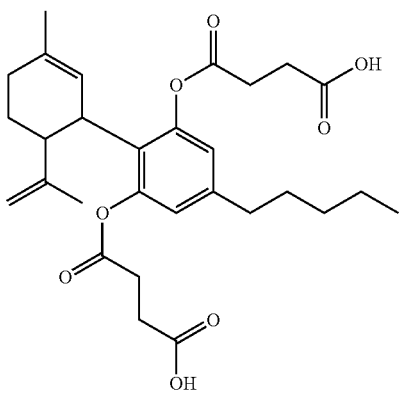

CBD-Di-Hemisuccinate
Chemical Formula: $C_{29}H_{38}O_8$
Molecular Weight: 514.62

Structure of CBD-Di-Hemisuccinate (CBD-Di-HS).

CBD was dissolved in DCM and catalytic amount of DMAP was added to it while stirring. Succinic anhydride (2.2 eq.) and triethylamine were added to CBD/DMAP solution. The reaction was stirred for 30 minutes. The product was purified using silica gel and eluted (in a gradient beginning at 0% EtOAc/100% Hexane and increasing to 75% EtOAc/25% Hexane) as pure compound. Product was confirmed by mass spectrometry.

Example 3: Synthesis of CBD-Di-Alaninate Ester

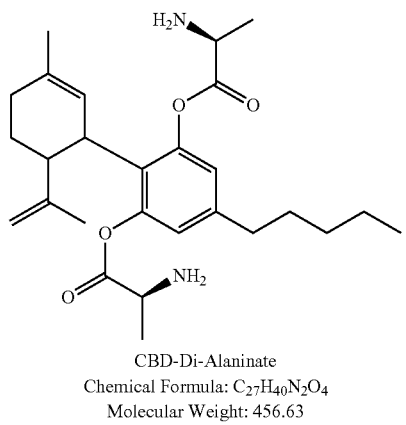 [SMILES: C=C(C)C1CCC(C)=CC1c1c(OC(=O)[C@H](C)N)cc(CCCCC)cc1OC(=O)[C@H](C)N]

CBD-Di-Alaninate
Chemical Formula: $C_{27}H_{40}N_2O_4$
Molecular Weight: 456.63

Structure of CBD-Di-Alaninate (CBD-Di-Ala).

A. Synthesis of CBD-Di-Ala-Boc

CBD was dissolved in DCM and catalytic amount of DMAP was added to it while stirring. Boc-alanine (2.2 eq.) was dissolved in DCM and 2.2 eq. of DCC was added to it while stirring. CBD/DMAP solution was added to Boc-alanine/DCC solution and allowed to stir for 30 minutes. Thin layer chromatography (10% EtOAc/90% Hexane; $R_f$=0.15) indicated the completion of reaction.

The product was purified using silica gel and product was eluted (in a gradient beginning at 0% EtOAc/100% Hexane and increasing to 15% EtOAc/85% Hexane) as pure compound.

B. Deprotection of CBD-Di-Ala-Boc to CBD-Di-Ala

CBD-di-Ala-boc was dissolved in THF while stirring. $HCl_{(g)}$ was bubbled through it for approximately 3 minutes while stirring. Excess $HCl_{(g)}$ was removed with $N_{2(g)}$ and the solvent was evaporated to dryness. Product was confirmed by mass spectrometry.

Example 4: Synthesis of CBD-Di-Alaninate-Di-Hemisuccinate

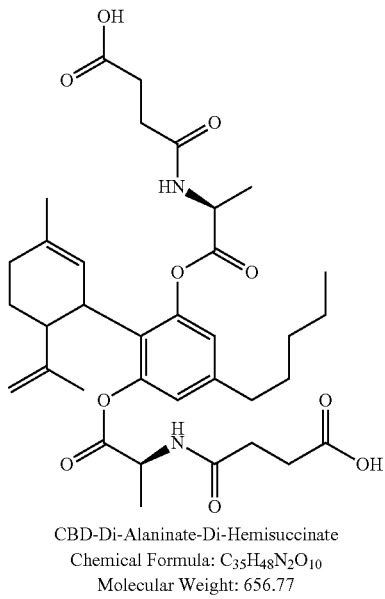 [SMILES: C=C(C)C1CCC(C)=CC1c1c(OC(=O)[C@H](C)NC(=O)CCC(=O)O)cc(CCCCC)cc1OC(=O)[C@H](C)NC(=O)CCC(=O)O]

CBD-Di-Alaninate-Di-Hemisuccinate
Chemical Formula: $C_{35}H_{48}N_2O_{10}$
Molecular Weight: 656.77

Structure of CBD-Di-Alaninate-Di-Hemisuccinate (CBD-Di-Ala-Di-HS).

CBD-Di-Ala was dissolved in DCM and catalytic amount of DMAP was added to it while stirring. Succinic anhydride (2.2 eq.) and triethylamine were added to CBD-Di-Ala/DMAP solution. The reaction was stirred overnight. The product was purified using silica gel and eluted (in a gradient beginning at 30% EtOAc/70% Hexane and increasing to 100% EtOAc/0% Hexane) as pure compound. Product was confirmed by mass spectrometry.

Example 5: Synthesis of CBD-Di-Valinate

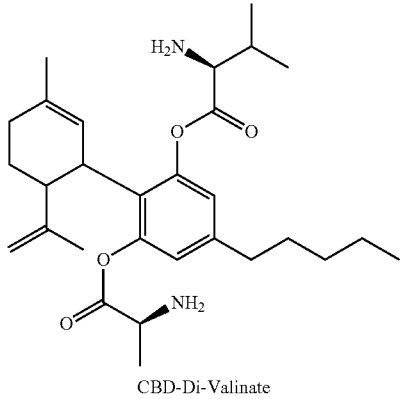

CBD-Di-Valinate
Chemical Formula: $C_{31}H_{48}N_2O_4$
Molecular Weight: 512.74

Structure of CBD-Di-Valinate (CBD-Di-Val).

A. Synthesis of CBD-Di-Val-Boc

CBD was dissolved in DCM and catalytic amount of DMAP was added to it while stirring. Boc-valine (2.2 eq.)

was dissolved in DCM and 2.2 eq. of DCC was added to it while stirring. CBD/DMAP solution was added to Boc-valine/DCC solution and allowed to stir for 5 minutes. Thin layer chromatography (10% EtOAc/90% Hexane) indicated the completion of reaction. The product was purified using silica gel and product was eluted (in a gradient beginning at 0% EtOAc/100% Hexane and increasing to 5% EtOAc/95% Hexane) as pure compound.

B. Deprotection of CBD-Di-Val-Boc to CBD-Di-Val

CBD-di-Val-boc was dissolved in THF while stirring. $HCl_{(g)}$ was bubbled through it for approximately 3 minutes while stirring. Excess of $HCl_{(g)}$ was removed with $N_{2(g)}$. Product was confirmed by mass spectrometry.

Example 6: Synthesis of CBD-Di-Valinate-Di-HS

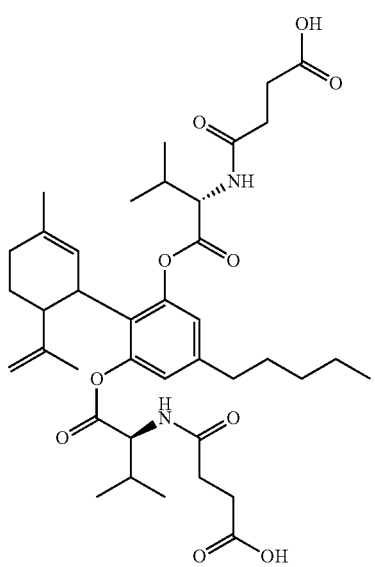

CBD-Di-Valinate-Di-Hemisuccinate
Chemical Formula: $C_{39}H_{56}N_2O_{10}$
Molecular Weight: 712.88

Structure of CBD-Di-Valinate-Di-Hemisuccinate (CBD-Di-Val-Di-HS).

CBD-Di-Val was dissolved in DCM and catalytic amount of DMAP was added to it while stirring. Succinic anhydride (2.2 eq.) and triethylamine were added to CBD-Di-Val/DMAP solution. The reaction was stirred overnight. The product was purified using silica gel and eluted (in a gradient beginning at 0% EtOAc/100% Hexane and increasing to 80% EtOAc/20% Hexane) as pure compound. Product was confirmed by mass spectrometry.

Example 7: Synthesis of CBD-Di-Hemiglutarate

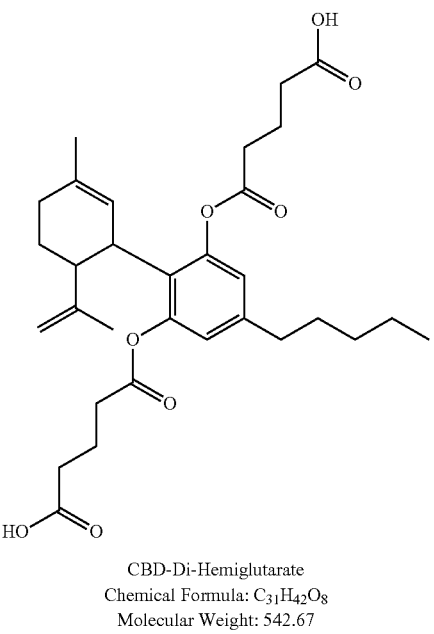 [SMILES: C=C(C)C1CCC(C)=CC1c1c(OC(=O)CCCC(=O)O)cc(CCCCC)cc1OC(=O)CCCC(=O)O]

CBD-Di-Hemiglutarate
Chemical Formula: $C_{31}H_{42}O_8$
Molecular Weight: 542.67

Structure of CBD-Di-Hemiglutarate (CBD-Di-HG).

CBD was dissolved in DCM and catalytic amount of DMAP was added to it while stirring. Glutaric anhydride (2.2 eq.) and triethylamine were added to CBD/DMAP solution. The reaction was stirred for 30 minutes. The product was purified using silica gel and eluted (in a gradient beginning at 0% EtOAc/100% Hexane and increasing to 40% EtOAc/60% Hexane) as pure compound. Product was confirmed by mass spectrometry.

Example 8: Synthesis of CBD-Mono-Valinate

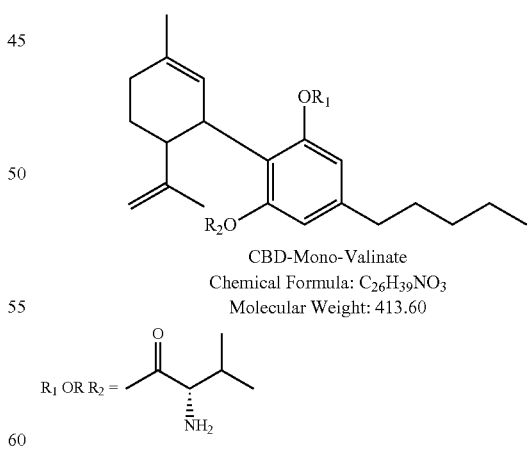

CBD-Mono-Valinate
Chemical Formula: $C_{26}H_{39}NO_3$
Molecular Weight: 413.60

Structure of CBD-Mono-Valinate (CBD-Mono-Val).

A. Synthesis of CBD-Mono-Val-Boc

CBD was dissolved in DCM and catalytic amount of DMAP was added to it while stirring. Boc-valine (1.1 eq.) was dissolved in DCM and 1.1 eq. of DCC was added to it while stirring. CBD/DMAP solution was added to Boc-valine/DCC solution and allowed to stir for 5 minutes. Thin layer chromatography (10% EtOAc/90% Hexane) indicated the completion of reaction. The product was purified using silica gel and product was eluted (in a gradient beginning at 0% EtOAc/100% Hexane and increasing to 3% EtOAc/97% Hexane) as pure compound.

B. Deprotection of CBD-Mono-Val-Boc to CBD-Mono-Val

CBD-Mono-Val-boc was dissolved in THF while stirring. $HCl_{(g)}$ was bubbled through it for approximately 2 minutes while stirring. Excess $HCl_{(g)}$ was removed with $N_{2(g)}$. Product was confirmed by mass spectrometry.

Example 9: Synthesis of CBD-Mono-Valinate-Mono-Hemisuccinate

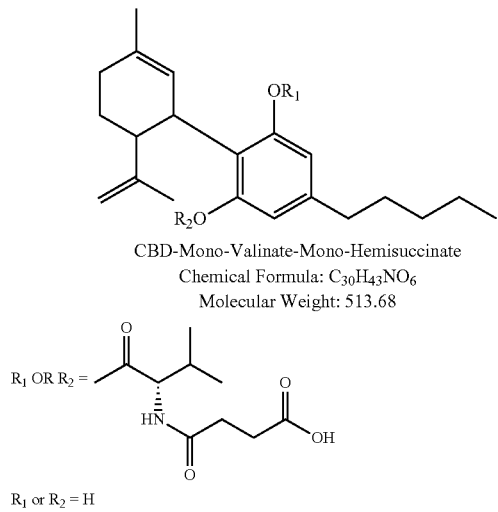

Structure of CBD-Mono-Valinate-Mono-Hemisuccinate (CBD-Mono-Val-Mono-HS).

C. Synthesis of CBD-Mono-Val-HS

CBD-Mono-Val was dissolved in DCM and catalytic amount of DMAP was added to it while stirring. Succinic anhydride (1.1 eq.) and triethylamine were added to CBD-Mono-Val/DMAP solution. The reaction was stirred overnight. The product was purified using silica gel and eluted (in a gradient beginning at 0% EtOAc/100% Hexane and increasing to 30% EtOAc/70% Hexane) as pure compound. Product was confirmed by mass spectrometry.

Example 10: Synthesis of CBD-Monovalinate-Dihemisuccinate (CBD-Mono-Val-Di-HS)

Synthesis of CBD-Mono-Val-Boc

CBD was dissolved in DCM and catalytic amount of DMAP was added to it while stirring. Boc-valine (1.1 eq.) was dissolved in DCM and 1.1 eq. of DCC was added to it while stirring. CBD/DMAP solution was added to Boc-valine/DCC solution and allowed to stir for 5 minutes. Thin layer chromatography (10% EtOAc/90% Hexane) indicated the completion of reaction. The product was purified using silica gel and product was eluted (in a gradient beginning at 0% EtOAc/100% Hexane and increasing to 3% EtOAc/97% Hexane) as pure compound.

B. Deprotection of CBD-Mono-Val-Boc to CBD-Mono-Val

CBD-Mono-Val-boc was dissolved in THF while stirring. $HCl_{(g)}$ was bubbled through it for approximately 2 minutes while stirring. Excess $HCl_{(g)}$ was removed with $N_{2(g)}$. Product was confirmed by mass spectrometry.

C. Synthesis of CBD-Mono-Val-diHS

CBD-Mono-Val was dissolved in DCM and catalytic amount of DMAP was added to it while stirring. Succinic anhydride (2.2 eq.) and triethylamine were added to CBD-Mono-Val/DMAP solution. The reaction was stirred overnight. The product was purified using silica gel and eluted (in a gradient beginning at 0% EtOAc/100% Hexane and increasing to 30% EtOAc/70% Hexane) as pure compound. Product was confirmed by mass spectrometry.

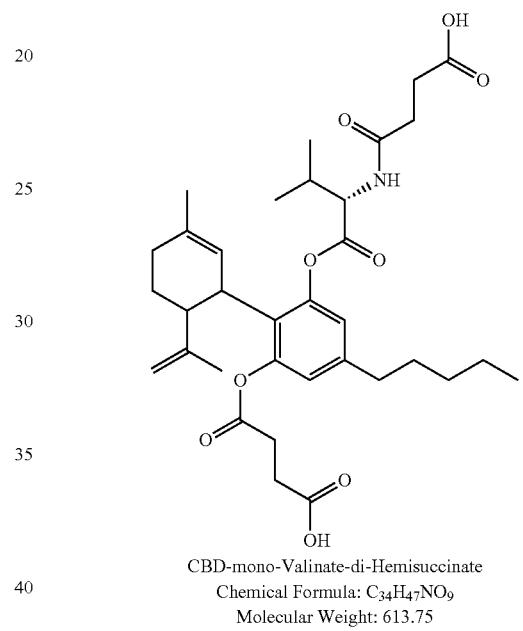

Example 11: Preparation of Topical Ophthalmic Formulations of Biologically Active CBD Analogs Formulations: 0.5% w/v CBD equivalent in Tocrisolve emulsion.

Tocrisolve composition: W/O emulsion composed of a 1:4 ratio of soya oil/water that is emulsified with the block co-polymer Pluronic F68. Manufacturing process for the Tocrisolve emulsion:

Add accurately weighed amount of drug a glass vial.

Add required volume of Torcisolve blank emulsion to each vial

Vortex each vial for 5 minutes.

Sonicate each vial for 10 minutes.

Centrifuge each vial for 5 minutes at 9000 rpm at 25° C.

Collect the supernatant and analyze for CBD, CBD-Val Mono and CBD-Val-HS mono as applicable.

Table 1 shows the solubility of CBD and CBD analogs in Tocrisolve emulsion.

TABLE 1

Solubility of CBD and its analogs in Tocrisolve ® emulsion.

|  | CBD | CBD-VAL-MONO (In terms of CBD) | CBD-VAL-HS-MONO (In terms of CBD) | CBD-HS (In terms of CBD) | CBD-VAL-HCl (In terms of CBD) | CBD-VAL-HS (In terms of CBD) |
|---|---|---|---|---|---|---|
| Maximum solubility achieved in Tocrisolve (% w/v) | 1.19 | 1.41 (1.07) | 1.18 (0.61) | 1.12 (0.7) | 2.04 (1.09) | 1.21 (0.53) |

Example 12: In Vivo Eye Tissue Levels of CBD and CBD Analogs 90 Min. After Topical Application of 50 µL of Formulations Containing the Equivalent of 250 µg of CBD in Tocrisolve® Emulsion Conscious male New Zeland albino rabbits were used. The formulations were applied topically into the rabbits eyes (50 µL containing the equivalent of 250 µg CBD) in Tocrisolve® emulsion formulations as described in Example 11. The animals were sacrificed 90 min. after drug application and the eye tissues harvested for analysis.

Table 2 shows the tissue levels (ng/g) following administration of CBD, CBD-Val-HCl and CBD-Val-HS.

The data showed that, while CBD and the water soluble CBD-Val-HCl only showed very low levels in the retina choroid, the CBD-Val-HS reached all tissues in high concentrations.

TABLE 2

Ocular tissue concentrations of CBD, CBD-Val and CBD-Val-HS (ng/gm of tissue); 90 min post topical application of CBD (0.47%), CBD-Val-HCl (0.94%) or CBD-Val-HS (1.2%) in Tocrisolve ® emulsion (Dose: 250 µg CBD; 50 µL instilled volume) respectively. ND-below detection limit.

| | Concentration (ng/gm of tissue); Dose in terms of CBD equivalent: 0.5% w/v & 50 µL: 250 µg | | | | | |
|---|---|---|---|---|---|---|
| | 0.5% w/v | 0.94% w/v CBD-Val-HCl | | 1.2% w/v CBD-Val-HS | | |
| Tissue | CBD | CBD | CBD-Val | CBD | CBD-Val | CBD-Val-HS |
| Retina Choroid | 17.3 ± 6.5 | ND | 9. ± 1.5 | ND | ND | 417 ± 114 |
| Aqueous Humor | ND | ND | ND | ND | ND | 24.6 ± 16.2 |
| Vitreous Humor | ND | ND | ND | ND | ND | 612 ± 264 |

Example 13: In Vivo Eye Tissue Levels of CBD VS Other Analogs of CBD

The same procedure was followed as shown under Example 12.

Additional CBD analogs were tested in this example. In this example the tissue levels of both free CBD and intact analog were determined. Results are shown in Table 3.

Formulations: Fifty microlitres of 0.5% w/v CBD in Tocrisolve emulsion (Dose: 0.25 mg)

Animal model: Conscious male new Zealand albino rabbits, Duration of the study: 90 min.

TABLE 3

Ocular tissue levels of both CBD and its analogs 90 min. following topical administration of the different analogs in Tocrisolve ® emulsion.

| | CBD-VAL-HS-MONO 0.97% w/v in Tocrisolve emulsion Set 1 | | CBD-VAL-MONO 0.65% w/v in Tocrisolve emulsion | | CBD 0.53% w/v in Tocrisolve emulsion | CBD-HS 0.81% w/v in Tocrisolve emulsion | |
|---|---|---|---|---|---|---|---|
| | Analog Conc. (ng/g of tissue) | CBD Conc. (ng/g of tissue) | Analog Conc. (ng/g of tissue) | CBD Conc. detected (ng/g of tissue) | CBD Conc. (ng/g of tissue) | Analog Conc. (ng/g of tissue) | CBD Conc. (ng/g of tissue) |
| AQ Humor | 90.3 ± 13.6 | ND | ND | ND | ND | ND | ND |
| Vitr. Humor | ND | ND | ND | ND | ND | ND | ND |
| Retina Choroid | 689 ± 127 | 194 ± 31.2 | ND | ND | ND | ND | 263 ± 132 |
| Iris Ciliary Bodies | 1034 ± 87.4 | 353 ± 43 | ND | ND | ND | ND | 267 ± 46 |

The data showed that while CBD and the free amino acid analogs showed no levels in the tissues at all, CBD-Val-HS reached both retina choroid and the iris-ciliary bodies but showed no detectable levels of CBD. On the other hand, CBD-mono-Val-HS was detected in high concentration in the aqueous humor, retina choroid and iris-ciliary bodies. Furthermore, the CBD-mono-Val-HS showed high levels of Free CBD in the retina choroid and iris-ciliary bodies.

Example 14: Comparison of the CBD and CBD-Analog Levels in the Ocular Tissues Following Topical Administration of the Two Biologically Active Analogs, Namely CBD-Di-Val-HS and CBD-Mono-Val-HS This example is a repeat of the experiment performed under Example 13 to show results reproducibility.

Sample preparation: Aqueous humor, Vitreous humor, Retina-Choroid and Iris-Ciliary bodies analysed for parent compound as well as CBD.

Formulations: Fifty microlitres of 0.5% w/v Tocrisolve emulsion formulations (Dose: 0.25 mg)

Animal model: Conscious male new Zealand albino rabbits, Duration of the study: 90 min

TABLE 4

Ocular tissue concentrations of CBD and CBD analogs 90 min post topical application of CBD-Val-HS-Mono or CBD-VAL-HS in Tocrisolve ® emulsion (Dose: 250 µg; 50 µL instilled volume) respectively. AH—aqueous humor, VH—Vitreous humor, RC—Retina-choroid, IC—Iris Ciliary bodies. ND—below detection limit.

| | 0.97% w/v in Tocrisolve emulsion CBD-VAL-HS-MONO Set 2 | | 1.2% CBD-VAL-HS Set 2 | |
|---|---|---|---|---|
| | Analog Concentration (ng/g of tissue) | CBD concentration (ng/g of tissue) | Analog Concentration (ng/g of tissue) | CBD concentration (ng/g of tissue) |
| Aqueous Humor | 98.7 ± 19.8 | 61.3 ± 5.9 | ND | ND |
| Vitreous Humor | ND | ND | ND | ND |
| Retina Choroid | 519 ± 476 | 503 ± 373 | 142 ± 76 | ND |
| Iris Ciliary Bodies | 422 ± 197 | 585 ± 103 | ND* | ND |
| Plasma | ND | ND | ND | ND |

*Only one of the animals showed 160 ng of CBD-Val-HS/g of tissue. The analog was below quantifiable levels in the other animals.

The data in Table 4 show similar results to those shown in Example 13 and prove that CBD-Mono-Val-HS is a superior analog for penetration into the different tissues of the eye. When biologically active analogs are designed such that R1 and R2 are natural amino acid residues (e.g. CBD-di-Val) or a dicarboxylic acid (e.g. CBD-di-HS) esters or the ester of the amino acid amide with a dicarboxylic acid (e.g. CBD-di-Val-di-HS), penetration into the ocular tissues is not adequate.

Only when the analog is a mono amino acid ester with the nitrogen of the amino acid in an amide linkage with a dicarboxylic acid, was the desired penetration to the inner chambers of the eye achieved.

Example 15: Bioavailability of CBD from Suppository Formulations Containing CBD-Di-Val-Di-HS (CBD-Val-HS)

CBD-Val-HS was formulated in both lipophilic (Wecobe W base) and hydrophilic (PEG 1000 base) suppository formulations. The formulations were administered to cannulated rats (100 mg suppository per rat) and blood samples were collected, centrifuged and the plasma separated for LC/MS/MS analysis. The amount of CBD in the plasma samples was quantified. The amount of CBD-Val-HS in the plasma samples was not quantified.

FIG. 1 shows the plasma levels of CBD vs. time following administration of 6.125 mg or 4.625 mg CBD-Val-HS in a lipophilic suppository (Wecobe W base).

FIG. 2 shows the plasma levels of CBD following the administration of 7 mg CBD-Val-HS in a hydrophilic base (PEG 1000).

Higher levels of CBD were achieved from a hydrophilic base containing CBD-Va-HS that when the same analog was delivered via a lipophilic base.

Example 16: Bioavailability of CBD-Mono-Val-Mono-Hemisuccinate (CBD-Mono-VHS) from a Lipophilic Suppository Formulation (Wecobee M)

CBD-Mono-Val-Mono-HS was formulated in Wecobee M suppository base (a triglyceride lipophilic base) at 75 mg/mL of melted base. The study was carried out in a cannulated rat model. Three animals were administered 100 µl. each of the semisolid formulation for a rectal dose of 7.5 mg CBD-Mono-VHS. This is followed by collection of blood samples (250 µl.) at each data point (0, 0.25, 0.5, 1, 2, 4, 6, and 24 hr.). The blood was centrifuged and the plasma was used for LC-MS/MS analysis. The results are shown in Table 5 and FIG. 3.

TABLE 5

Plasma Concentration of CBD-Mono-VHS for Individual Animals over Time Post Administration of 7.5 mg of the Drug in a Lipophilic (Wecobee M) Suppository Form in Rats

| Time (Hrs.) | 0 | 0.25 | 0.5 | 1 | 2 | 4 | 6 | 24 |
|---|---|---|---|---|---|---|---|---|
| Animal 1 | 0.0 | 3.9 | 12.8 | 13.8 | 14.5 | 27.5 | 41.6 | N/A |
| Animal 2 | 0.0 | 7.1 | 11.6 | 18.5 | 34.6 | 45.1 | 53.0 | 44.3 |
| Animal 3 | 0.0 | 7.1 | 9.0 | 14.1 | 12.7 | 22.0 | 24.8 | 7.3 |
| Average | 0.0 | 6.0 | 11.1 | 15.5 | 20.6 | 31.5 | 39.8 | 17.2 |

Example 17: Bioavailability of CBD-Mono-Val-Mono-Hemisuccinate (CBD-Mono-VHS) from a Hydrophilic Suppository Formulation (Polyethylene Glycol 1000, PEG 1000)

CBD-Mono-Val-Mono-HS was formulated in PEG 1000 suppository base (a hydrophilic suppository base) at 75 mg/mL of melted base. The study was carried out in a cannulated rat model. Three animals were administered 100 µl. each of the semisolid formulation for a rectal dose of 7.5 mg CBD-Mono-VHS. This is followed by collection of blood samples (250 µl.) at each data point (0, 0.25, 0.5, 1, 2, 4, 6, and 24 hr.). The blood was centrifuged and the plasma was used for LC-MS/MS analysis. The results are shown in Table 6 and FIG. 4.

TABLE 6

Plasma Concentration of CBD-Mono-VHS for Individual Animals over Time Post Administration of 7.5 mg of the Drug in a Hydrophilic (PEG 1000) Suppository Form in Rats

| Time (Hrs.) | 0 | 0.25 | 0.5 | 1 | 2 | 4 | 6 | 8 | 24 |
|---|---|---|---|---|---|---|---|---|---|
| Animal 1 | 0.0 | 10.1 | 38.4 | 54.3 | 123.0 | 60.5 | 37.4 | 21.6 | 2.5 |
| Animal 2 | 0.0 | 14.8 | 32.9 | 108.0 | 113.0 | 53.5 | 30.1 | 27.3 | 2.6 |
| Animal 3 | 0.0 | 14.7 | 44.2 | 106.0 | 108.0 | 57.5 | 18.6 | 44.8 | 0.0 |
| Average | 0.0 | 13.2 | 38.5 | 89.4 | 114.7 | 57.2 | 28.7 | 24.0 | 0.9 |

Example 18. Oral Bioavailability of CBD-Mono-Val-Mono-Hemisuccinate (CBD-Mono-VHS)

CBD-Mono-VHS was formulated in a sesame seed oil (Welch, Holme and Clark Co. lot #39375) formulation composed of 40 mg/mL solution of the drug substance/ml. Animals (cannulated rats, n=4) were dosed 100 μl of the oil solution by oral gavage. Blood samples were collected at 0, 0.25, 0.5, 1, 2, 4, 6, 8, and 24 hr. after dosing. The blood samples were centrifuged and the plasma was analyzed for CBD-Mono-VHS. Table 7 and FIG. 5 show the results, with very high blood levels which remain significant (>10 ng/mL) at 24 hr. after dosing.

TABLE 7

Plasma Concentration of CBD-Mono-VHS for Individual Animals Post Oral Administration of a 4 mg/animal Dose of the Drug

| Time (Hrs.) | 0 | 0.25 | 0.5 | 1 | 2 | 4 | 6 | 8 | 24 |
|---|---|---|---|---|---|---|---|---|---|
| Animal 1 | 0.0 | 1512.3 | 2655.0 | 3120.9 | 1317.3 | 423.3 | 181.0 | 89.8 | 37.8 |
| Animal 2 | 0.0 | 370.2 | 1437.1 | 2496.6 | 399.5 | 116.1 | 397.8 | 210.0 | 47.1 |
| Animal 3 | 0.0 | 978.0 | 1238.2 | 1492.0 | 264.8 | 284.8 | 197.8 | 264.4 | 17.5 |
| Animal 4 | 0.0 | 1255.5 | 1174.8 | 1400.6 | 392.2 | 115.1 | 71.4 | 44.6 | 6.5 |
| Average | 0.0 | 1029.0 | 1626.3 | 2127.5 | 593.5 | 234.8 | 212.0 | 152.2 | 27.2 |

Example 19. Organ Distribution of CBD-Mono-VHS after Oral Administration

To determine whether CBD-Mono-VHS reaches the organs and especially the brain, two cannulated rats were administered same dose as those in Example 18. One rat was sacrificed at 2 hr. after dosing and the other at 4 hr. after dosing and the organs were harvested (brain, liver, and spleen) as well as blood for analysis. Table 8a shows the organ levels of CBD-Mono-VHS at 2 and 4 hrs. after oral dosing (4 mg/animal) while Table 8b shows the plasma levels.

The data are depicted in FIGS. 6a and 6b.

The plasma levels were consistent with the data from Example 18 and the organs showed high levels of the drug indicating effective bioavailability.

TABLE 8a

Organ levels of CBD-Mono-VHS at 2 and 4 hr. after oral dosing with 4 mg/animal.
CBD-Mono-Val-Mono-HS

| Time | Organ | Conc. (ng/organ) |
|---|---|---|
| 2 HR | BRAIN | 556 |
|  | LIVER | 66484 |
|  | KIDNEY | 353 |
|  | SPLEEN | 1438 |
| 4 HR | BRAIN | 205 |
|  | LIVER | 8301 |
|  | KIDNEY | 115 |
|  | SPLEEN | 392 |

TABLE 8b

Plasma levels at 2 and 4 hr. after oral dosing with 4 mg/animal of CBD-Mono-VHS.
CBD-Mono-Val-Mono-HS (Plasma)

| Time | Conc. (ng/mL) |
|---|---|
| 2 HR | 285 |
| 4 HR | 53 |

Example 20. Stability of CBD-Mono-Val-Mono-Hemisuccinate (CBD-Mono-VHS) in Simulated Gastric Juice and Intestinal Juice CBD is known to convert, at least partially, to $\Delta^9$-THC (the psychoactive component of *cannabis*) and to other cannabinoids under the acidic conditions of the stomach. (Watanabe, K., Itokawa, Y., Yamaori, S., Funahashi, T., Kimura, T., Kaji, T., Usami, N., Yamamoto, I., 2007; Conversion of cannabidiol to $\Delta^9$-tetrahydrocannabinol and related cannabinoids in artificial gastric juice, and their pharmalogical effects in mice, Forensic Toxicol, 25, 16-21. and Merrick, J., Lane, B., Sebree, T., Yaksh, T., O'Neill, C., Banks, S., 2016; Identification of Psychoactive Degradants of Cannabidiol in Simulated Gastric and Physiological Fluid, *Cannabis* and Cannabinoid Research, 1.1, 102-112). This results in side effects that are proportional to the degree of conversion.

The stability CBD and CBD analogs (CBD-Mono-VHS and CBD-Di-VHS) was evaluated under acidic and alkaline conditions to simulate exposure to gastric and intestinal fluids. The procedure is outlined as follows:
1. Stock solution of 5 mg/mL CBD, CBD-Mono-Val-Mono HS, CBD-Di-Val-Di HS was prepared.
2. Simulated Gastric Fluid (pH 1.2)+1% (SDS) was prepared and kept in 37° C. water bath.

3. Physiological buffer (pH 7.4)+1% SDS was prepared and kept in 37° C. water bath.
4. 100 μL of CBD, CBD-Mono-Val-Mono HS or CBD-Di-Val-Di-HS stock in acetonitrile (equivalent to 500 μg) was spiked into separate vials containing 5 ml of either pH 1.2 and 7.4.
5. At each time point, 100 μL of the solution was withdrawn.
6. 900 μL acetonitrile was added to each sample.
7. All samples centrifuged at 4° C. and 13,000 rpm.
8. 100 μL of the supernatant was withdrawn; to this 100 μL of supernatant, 900 μL of acetonitrile was added and placed in LC vials for analysis.

Tables 9, 10 and 11, and FIGS. 7a, 7b, 18, and 19 show the results.

CBD converts to $\Delta^9$-THC under acidic conditions while CBD analogs of this invention do not produce $\Delta^9$-THC.

TABLE 9

Concentration (ng/ml) of CBD and $\Delta^9$-THC, at different incubation times at 37° C. and at pH's of 1.2 and 7.4

| | Acid (pH 1.2) | | | | Base (pH 7.4) | |
|---|---|---|---|---|---|---|
| | CBD | | $\Delta^9$-THC | | | CBD |
| Time Point | Peak Area | Conc. | Peak Area | Conc. | Time Point | Peak Area | Conc. |
| 0 | 1578900 | 656 | 70146 | 38 | 0 | 1816000 | 760 |
| 15 | 1343400 | 553 | 433990 | 238 | 15 | 2233800 | 943 |
| 30 | 546430 | 204 | 442900 | 243 | 30 | 2397500 | 1015 |
| 60 | 335800 | 111 | 904900 | 496 | 60 | 263670 | 1119 |
| 90 | 288960 | 91 | 1141200 | 625 | 90 | 2549800 | 1081 |
| 120 | 186660 | 46 | 829150 | 454 | 120 | 2307100 | 975 |

Conclusion: CBD is partially converted to THC under the acidic conditions of the gastric juice, but stable under the physiologic pH of 7.4.

TABLE 10

Concentration (ng/ml) of CBD-Mono-Val-Mono-HS at different time points post incubation at pH's of 1.2 and 7.4 at 37° C.

| | Acid (pH 1.2) | | | Base (pH 7.4) | |
|---|---|---|---|---|---|
| | CBD-Mono-Val-Mono-HS | | | CBD-Mono-Val-Mono-HS | |
| Time Point | Peak Area | Conc. | Time Point | Peak Area | Conc. |
| 0 | 1515300 | 941 | 0 | 1424000 | 886 |
| 15 | 2246500 | 1380 | 15 | 2345100 | 1439 |
| 30 | 2400300 | 1472 | 30 | 1941900 | 1197 |
| 60 | 2579800 | 1579 | 60 | 2932900 | 1791 |
| 90 | 2411300 | 1478 | 90 | 2639800 | 1615 |
| 120 | 2479500 | 1519 | 120 | 2833100 | 1731 |

Conclusion: CBD-Mono-VHS is stable under both acidic (gastric juice) conditions and intestinal (pH 7.4) juice conditions.

TABLE 11

Concentration (ng/ml) of CBD-Di-Val-Di-HS at different time points post incubation at pH's of 1.2 and 7.4 at 37° C.

| | Acid (pH 1.2) | | | Base (pH 7.4) | |
|---|---|---|---|---|---|
| | CBD-Di-Val-Di-HS | | | CBD-Di-Val-Di-HS | |
| Time Point | Peak Area | Conc. | Time Point | Peak Area | Conc. |
| 0 | 454560 | 754 | 0 | 488890 | 794 |
| 15 | 1346800 | 1797 | 15 | 549120 | 865 |
| 30 | 1091200 | 1498 | 30 | 776690 | 1131 |
| 60 | 1418400 | 1881 | 60 | 1004900 | 1397 |
| 90 | 1403700 | 1863 | 90 | 994740 | 1386 |
| 120 | 1420400 | 1883 | 120 | 855710 | 1223 |

Conclusion: CBD-DiVal-DiHS is stable under acidic juice conditions and the physiologic (pH 7.4) intestinal juice conditions.

Example 21. Bioavailability of CBD from Suppository Formulations Containing CBD-Hemiglutarate (CBD-HG)

CBD-Hemiglutarate was formulated in a lipophilic suppository base (Wecobee M) at 75 mg/mL of molten base. Doses of 100 μl. of the formulation were administered rectally (equivalent to 7.5 mg dose/animal) to cannulated rats (n=4). Blood samples (0.25 mL) were collected at 0, 0.25, 0.5, 1, 2, 4, 6, 8, and 24 hr. after dosing. After centrifugation of the blood, plasma was collected (100 μl.) and subjected to LC-MS/MS analysis for CBD. The amount of CBD-HG in the plasma was not determined. Table 12 and FIG. 10 show the results.

TABLE 12

Plasma Concentration of CBD Following Rectal Administration of CBD-Hemiglutarate (7.5 mg dose) in a Lipophilic Suppository Formulation

| Time (Hrs.) | 0 | 0.25 | 0.5 | 1 | 2 | 4 | 6 | 8 | 24 |
|---|---|---|---|---|---|---|---|---|---|
| Animal 1 | 0 | 27.8 | 29 | 5.92 | 18.8 | 15.8 | 0 | 0 | 0 |
| Animal 2 | 0 | 0 | 42.3 | 8.65 | 0 | 7.45 | 0 | 0 | 0 |
| Animal 3 | 0 | 0 | 44.3 | 17 | 16.8 | 6.63 | 0 | 0 | 0 |
| Animal 4 | 0 | 14.5 | 6.16 | 11.5 | 26.2 | 7.43 | 0 | 0 | 0 |
| Average | 0 | 10.575 | 30.44 | 10.7675 | 15.45 | 9.3275 | 0 | 0 | 0 |

Example 22. Plasma and Organ Concentrations of CBD and CBD-Mono-VHS Following IP Administration of CBD-Mono-VHS in Mice CBD-Mono-VHS was administered intraperitoneally to mice at 2 doses (30 μg and 60 μg equivalent of CBD/mouse). Seventy minutes after dosing the animals (3 mice in each dose group), all animals were sacrificed. Blood, as well as organs (liver, spleen, kidney, and brain), were harvested for LC-MS/MS analysis of their content of both CBD and CBD-Mono-VHS.

Table 13 shows the total CBD-Mono-VHS content of each organ for each animal for both doses with average and standard deviation, while Table 14 shows the total CBD content. Also shown is the concentration of CBD-Mono-VHS in the plasma 70 minutes after dosing.

Figure 11B:
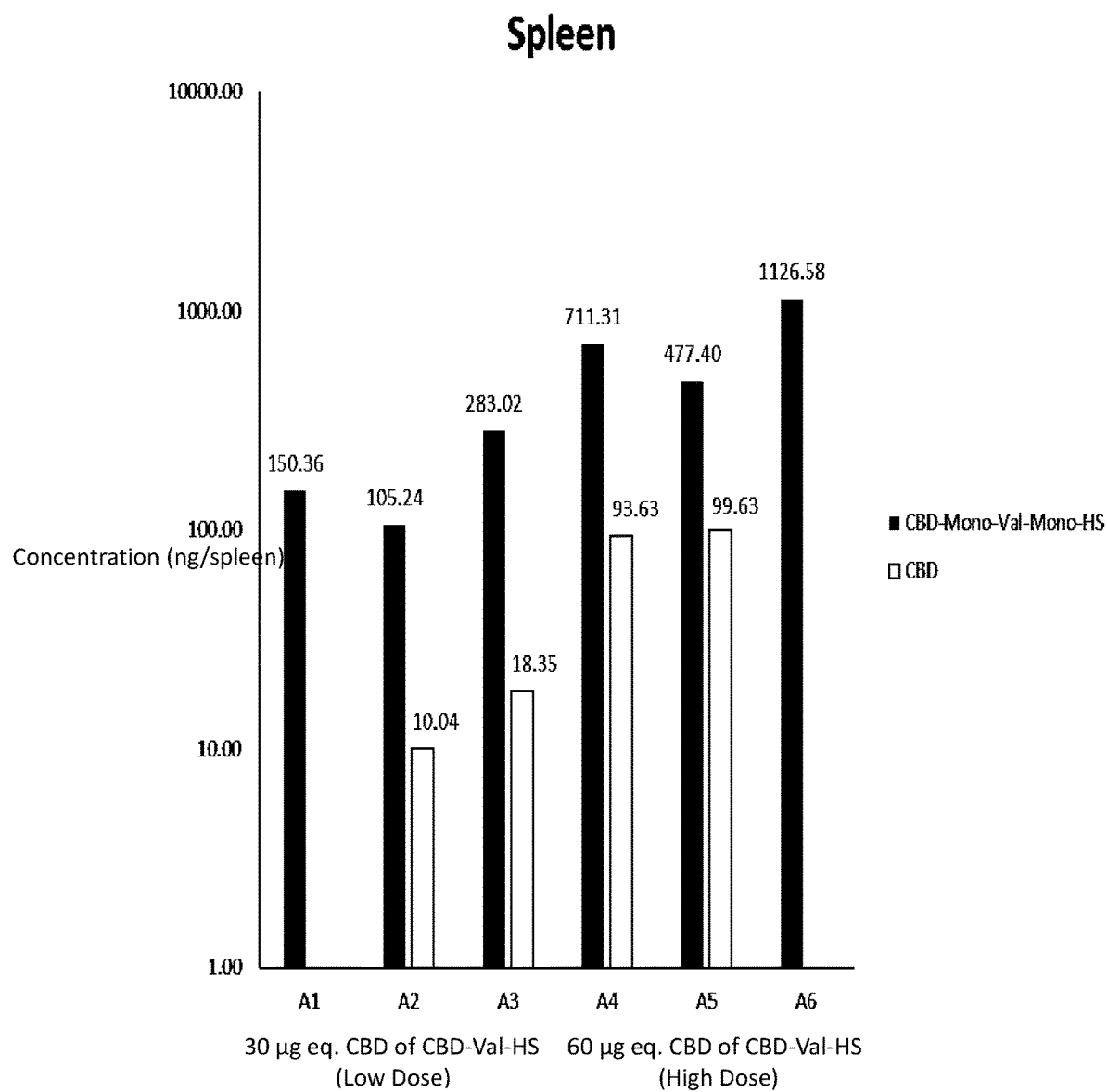
Figure 11C:
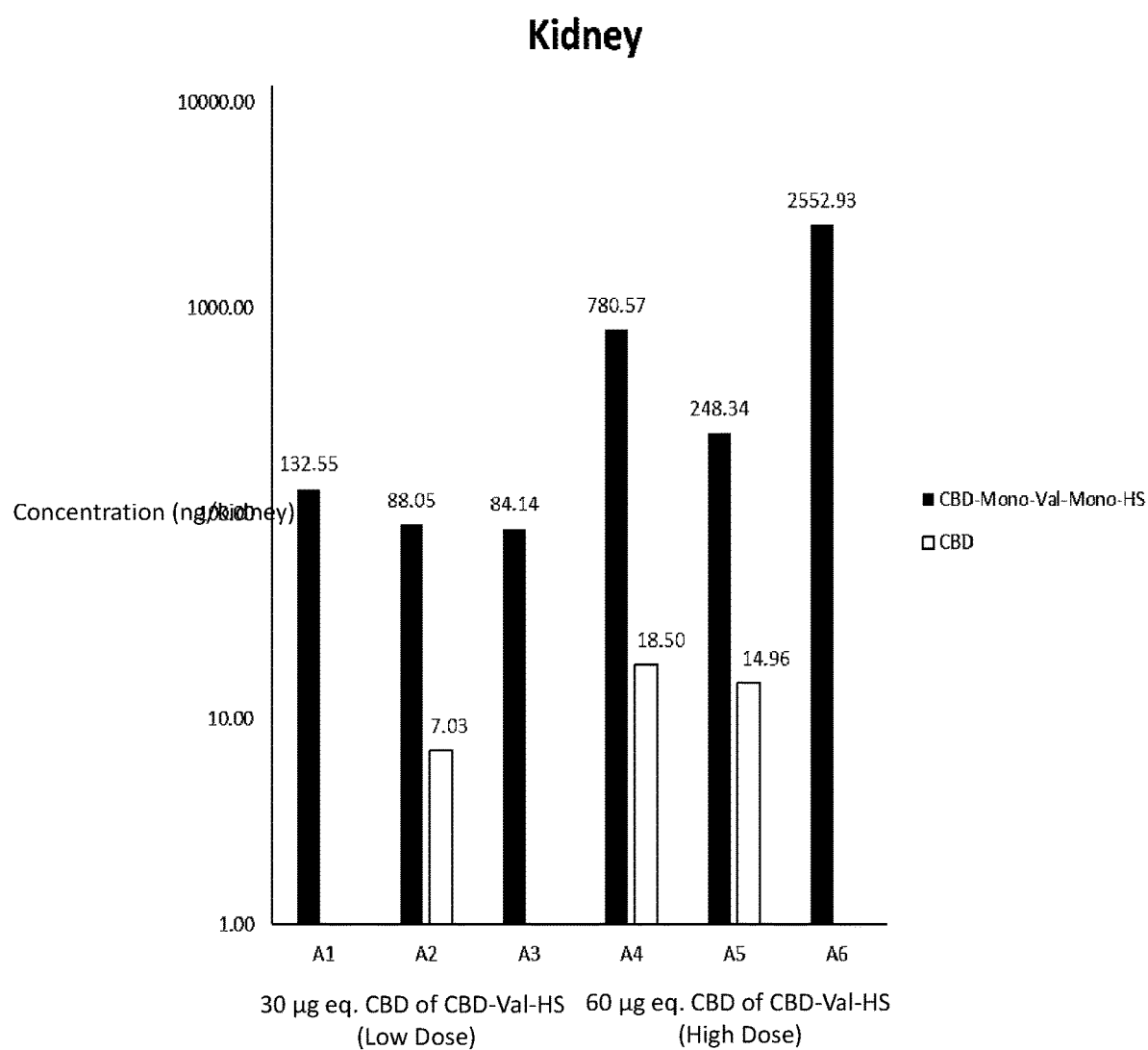
Figure 11D:
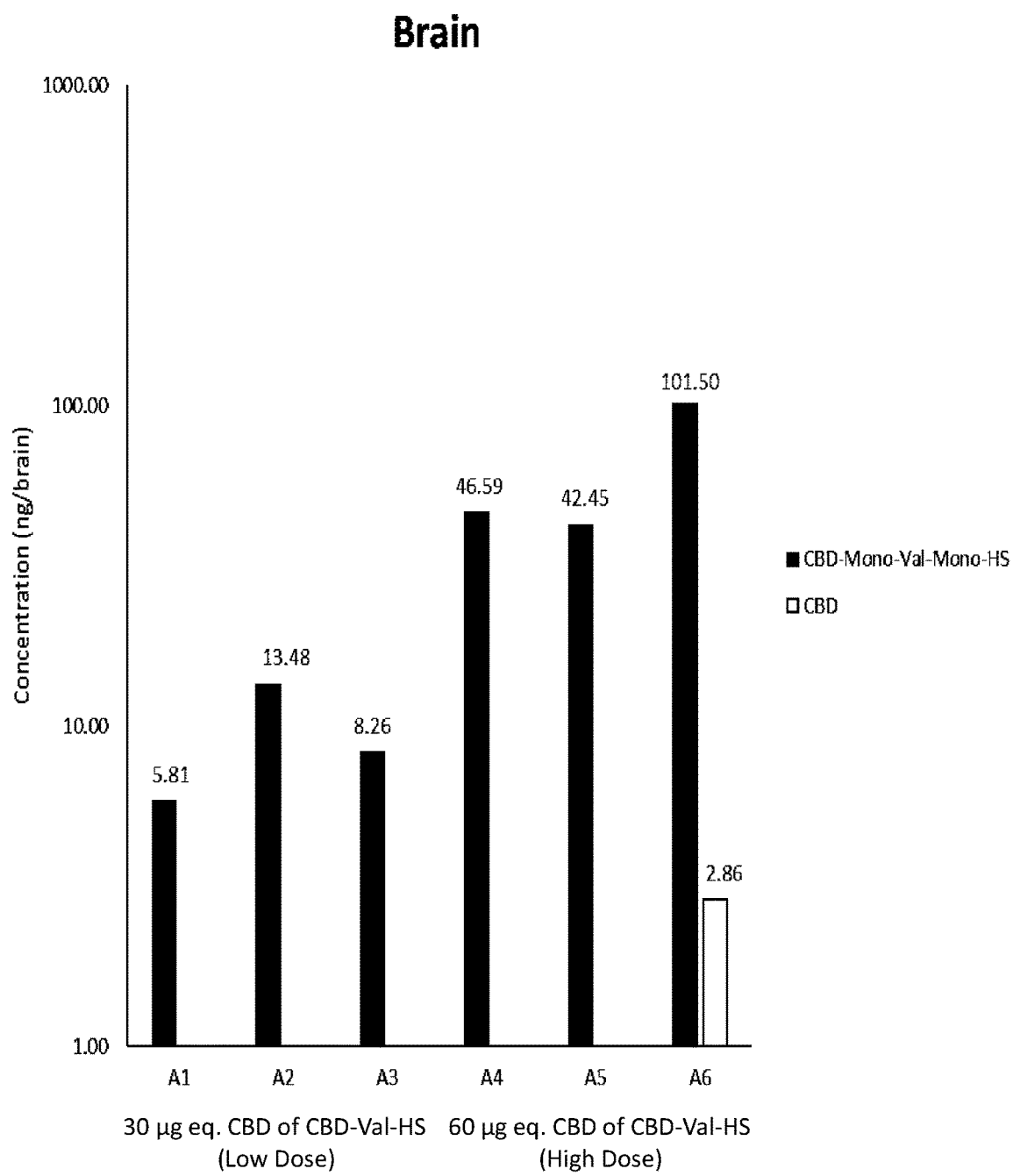

The results are also depicted in FIG. 11a (liver), FIG. 11b (spleen), FIG. 11c (kidney), FIG. 11d (brain), and FIG. 12 (plasma concentration (ng/mL)) for individual animals from each dose.

Conclusion: IP administration of CBD-Mono-VHS in mice results in high concentrations of the drug in all organs tested in a dose proportional manner. More importantly, the compound crosses the blood brain barrier, a significant finding in the use of this compound for the treatment of CNS based disease conditions.

TABLE 13

Total Drug Load (in ng) of CBD-Mono-Val-Mono-HS in the Different Organs and the Plasma Concentrations (ng/mL) 70 Minutes Post IP Administration of Two Dose Levels (30 and 60 μg./animal) of the Drug

| | | Total CBD-Mono-Val-Mono-HS (ng)* | | | | | |
|---|---|---|---|---|---|---|---|
| Dose | Animal # | Liver | Kidney | Spleen | Brain | Plasma | Total |
| Low | 1 | 1543.96 | 132.55 | 150.36 | 5.81 | 22.97 | 1855.656 |
| Dose | 2 | 1431.98 | 88.05 | 105.24 | 13.48 | 32.08 | 1670.831 |
| (30 μg | 3 | 534.11 | 84.14 | 283.02 | 8.26 | 32.24 | 941.765 |
| CBD/ | AVG. | 1170.01 | 101.58 | 179.54 | 9.18 | 29.10 | 1489.42 |
| mouse) | SD | 553.55 | 26.89 | 92.41 | 3.92 | 5.31 | 483.20 |
| High | 4 | 8380.90 | 780.57 | 711.31 | 46.59 | 137.82 | 10057.18 |
| Dose | 5 | 2882.40 | 248.34 | 477.40 | 42.45 | 100.53 | 3751.113 |
| (60 μg | 6 | 11413.38 | 2552.93 | 1126.58 | 101.50 | 393.00 | 15587.4 |
| CBD/ | AVG. | 7558.89 | 1193.95 | 771.76 | 63.51 | 210.45 | 9798.56 |
| mouse) | SD | 4324.489 | 1206.627 | 328.787 | 32.96302 | 159.1886 | 5922.379 |

*The organ levels are total content of CBD-Mono-VHS in the entire organ while the plasma content is in ng/ml.

TABLE 14

Total Drug Load (in ng) of CBD in the Different Organs and the Plasma Concentrations (ng/mL) 70 Minutes Post IP Administration of Two Dose Levels (30 and 60 μg/animal) of the Drug

| | | Total CBD (ng) | | | | | |
|---|---|---|---|---|---|---|---|
| Dose | Animal # | Liver | Kidney | Spleen | Brain | Plasma | Total |
| Low | 1 | 81.42 | 0.00 | 0.00 | 0.00 | 0.00 | 81.42 |
| Dose | 2 | 41.82 | 7.03 | 10.04 | 0.00 | 0.00 | 58.89 |
| (30 μg | 3 | 19.61 | 0.00 | 18.35 | 0.00 | 0.00 | 37.96 |
| CBD/ | AVG. | 47.62 | 2.343 | 9.46 | 0.00 | 0.00 | 59.42 |
| mouse) | SD | 25.56 | 3.31 | 7.50 | 0.00 | 0.00 | 21.73 |
| High | 4 | 319.91 | 18.50 | 93.63 | 0.00 | 0.00 | 432.04 |
| Dose | 5 | 195.66 | 14.96 | 99.63 | 0.00 | 0.00 | 310.25 |
| (60 μg | 6 | 369.75 | 0.00 | 0.00 | 2.86 | 0.00 | 372.61 |
| CBD/ | AVG. | 295.11 | 11.15 | 64.42 | 0.95 | 0.00 | 371.63 |
| mouse) | SD | 73.20 | 8.02 | 45.62 | 1.35 | 0.00 | 60.90 |

In a further embodiment of the present invention the inventors explored whether cannabidiol (CBD) or biologically active CBD analogs possessed analgesic properties alone and in combination of a sub-analgesic dose of or morphine in a mouse model of cisplatin induced neuropathy. Mice received 12 alternating days of 2.3 mg/kg cisplatin and Ringers solution IP. An electronic Von Frey quantified the development of tactile allodynia before, during and after the cisplatin protocol and served as the endpoint for analgesic screening. Test articles given alone or in combination included, vehicle, morphine (0.5 and 2.5 mg/kg) and CBD (1.0 and 2.0 mg/kg in Experiment 1) or a CBD analog (1.0-4.0 mg/kg in Experiment 2) and were given IP 45 m before testing. Six dosings of cisplatin produced robust tactile allodynia that was attenuated by 2.5 mg/kg morphine. CBD produced a modest attenuation of tactile allodynia that was potentiated by sub-analgesic doses of morphine. The biologically active CBD analog produced a robust attenuation of tactile allodynia equivalent to morphine; this effect was reproduced at lower doses when given in combination of sub-analgesic doses of morphine. These findings suggest that a biologically active CBD analog may be an effective pain management strategy for neuropathy associated with chemotherapy in oncology settings Example 23: Efficacy of CBD in a Cisplatin-Induced Tactile Allodynia Model Subjects Male C57BL/6 mice (25-30 g; Envigo; Indianapolis, Ind.) were housed 5 per polycarbonate tub with soft bedding in a temperature and humidity controlled vivarium. Mice were maintained under a 12-hour light/dark cycle with lights on at 06:00. Food and water were available ad libitum. Animals acclimated to the vivarium 1 week prior to experimental manipulations. All experimental procedures were approved by the Institutional Animal Care and Use Committee at the University of Mississippi (Protocols 13-017 and 15-022).

Behavioral Measures

An electronic von Frey (eVF; Topcat Metrology Ltd; Little Downham, UK) quantified the development of tactile allodynia during CIN induction and served as the endpoint in analgesic screening. Animals were placed into an elevated clear Plexiglas enclosure (3.81×11.43×11.43 cm) with a metal rod floor. After an acclimation period of 15 min, a von Frey filament was applied to the mid plantar region of the hind paw and withdrawal thresholds were recorded. Filaments were applied to alternating left and right hind paws at 3 min intervals for a total of 4 measurements per paw. The average score of these 8 tests served as the dependent measure.

Test Articles

Cisplatin (Tocris; Ellisville, Mo.) was dissolved in 0.9% saline to yield dosages 2.3 mg/kg/ml. Lactated Ringer's solution (0.25 mL; Abbott laboratories; Chicago, Ill.) was used to hydrate mice to prevent kidney and liver damage associated with repeated cisplatin administration. Morphine sulfate (Research Biochemicals International; Natick, Mass.) was dissolved in 0.9% saline to yield dosages of 0.1 and 2.5 mg/kg/ml. CBD 1.0 and 2.0 mg/kg/mL (ELI Laboratories; Oxford, Miss.) solutions, dissolved in 5% ethanol, 5% Cremophor and injectable water. All test articles were administered intraperitoneally (IP).

Cisplatin Induction and Drug Efficacy Screening Procedure

Mice received 6 IP injections of cisplatin (2.3 mg/kg/mL) on alternating days with lactated Ringer's solution on intervening days over a 12-day period. Baseline eVF measurements were taken prior to enrollment in the study to ensure balanced group assignments. To monitor the progression of tactile allodynia additional eVF measurements were taken on Ringers Day 3 and 6 prior to daily injections. On Ringers Day 6, eVF measurements revealed significantly lower paw withdrawal thresholds indicative of neuropathy. Drug efficacy screening was conducted 2 days later to minimize the potential effect that repeated eVF testing may have on our CIN endpoint. Mice were counterbalanced and assigned to drug groups. All test compounds were delivered IP 45 minutes prior to eVF testing.

Results and Discussion

The effects of the various test articles on cisplatin-induced tactile allodynia are summarized in FIG. 13. Baseline eVF responses prior to and after cisplatin administration are shown as dashed lines. Following the cisplatin induction protocol, all mice showed lower response thresholds indicative of tactile allodynia. A 1-way ANOVA of these data revealed a significant decrease in paw withdrawal following the cisplatin protocol, $F(1.71)=136.03$, $p<0.0001$.

On drug efficacy screening day, vehicle-treated mice continued to show tactile allodynia. A sub-analgesic dose of morphine (0.1 mg/kg) did not affect eVF responses whereas the 2.5 mg/kg morphine fully attenuated tactile allodynia. CBD produced a modest attenuation of CIN at 1.0 but not at the 2.0 mg/kg doses. The sub-analgesic dose of morphine given in combination with 2.0 mg/kg CBD attenuated tactile allodynia comparable to 2.5 mg/kg morphine. This CBD-opioid synergistic effect was not further enhanced with 2.5 mg/kg morphine.

A 1-way ANOVA of these data revealed a significant main effect for Drug, $F(7.71)=15.72$, $p<0.0001$. Fisher's LSD demonstrated that the mean withdrawal thresholds were significantly higher than vehicle in 2.5 mg/kg morphine, 1.0 mg/kg CBD, 0.1 mg/kg morphine in combination with 1.0 and 2.0 mg/kg CBD, and 2.5 mg/kg morphine in combination with 2.0 mg/kg CBD groups ($ps \leq 0.0001$).

These results demonstrate that a 6-dosing protocol of 2.3 mg/kg cisplatin over a 12-day period leads to robust tactile allodynia in mice, a hallmark sign of chemotherapy-induced neuropathy. Further, tactile allodynia persisted for several days after the last cisplatin administration as evidenced by continued reduced paw withdrawal thresholds in vehicle-treated mice on drug efficacy screening day. These findings are consistent with the literature that this and other cisplatin administration protocols produce CIN in rodents (Park et al., 2012; Guidon et al., 2012).

Mice receiving 2.5 mg/kg morphine displayed a robust attenuation of tactile allodynia. This finding is consistent with the literature that opioid agonists produce analgesia in a wide variety of pain models including CIN (Guidon et al., 2012). Mice receiving 1.0 mg/kg CBD displayed a modest but significant attenuation of tactile allodynia. A higher dose of CBD was ineffective in the model. A sub-analgesic dose of morphine (0.1 mg/kg) did not further alter the anti-allodynic properties of 1.0 mg/kg CBD given alone. However, this sub-analgesic dose of morphine greatly enhanced the efficacy of 2.0 mg/kg CBD producing an effect equivalent to that of 2.5 mg/kg dose of morphine alone. Finally, the effective morphine dose of 2.5 mg/kg did not further potentiate the 2.0 mg/kg CBD. Collectively, these findings demonstrate that the modest efficacy of CBD can be greatly enhanced with sub-analgesic doses of an opioid agonist.

Example 24: Efficacy of CBD-Mono-VHS in a Cisplatin-Induced Tactile Allodynia Model Methods Subjects, behavior cisplatin injection protocol, and behavioral measures were as described in Example 23. As before, morphine sulfate was dissolved in 0.9% saline to yield dosages of 0.1 and 2.5 mg/kg/ml. Cannabidiol-mono-val-mono-hemisuccinate (CBD-Mono-VHS; ELI Laboratories; Oxford, Miss.) 1.0 to 4.0 mg/kg/mL was dissolved in 5% ethanol, 5% Cremophor and injectable water and are dose-equivalent in terms of CBD equivalent. The full doses of CBD-Mono-VHS were 1.6 to 6.4 mg/kg. All test articles were administered intraperitoneally (IP). All experimental procedures were approved by the Institutional Animal Care and Use Committee at the University of Mississippi (Protocol 15-022).

Results and Discussion

Efficacy screening of these test articles on cisplatin-induced tactile allodynia are summarized in FIG. 14. Baseline eVF responses prior to and after cisplatin administration are shown as dashed lines. Following the cisplatin induction protocol, all mice showed lower response thresholds indicative of tactile allodynia. A 1-way ANOVA of these data revealed a significant decrease in paw withdrawal following the cisplatin protocol, $F(1.99)=601.36$, $p<0.0001$.

On drug efficacy screening day, vehicle-treated mice continued to show tactile allodynia. A sub-analgesic dose of morphine (0.1 mg/kg) did not affect eVF responses whereas the 2.5 mg/kg morphine fully attenuated tactile allodynia. CBD-Mono-VHS given alone produced a dose-dependent attenuation of tactile allodynia that equal 2.5 mg/kg morphine at 3.0 and 4.0 mg/kg. The combination of a sub-analgesic dose of morphine and CBD-Mono-VHS shifted this dose response curve to the left where 2.0 mg/kg CBD-Mono-VHS attenuated tactile allodynia equal to that of 2.5 mg/kg morphine.

Consistent with these findings, a 1-way ANOVA of these data revealed a significant effect for Drug, $F(10.99)=9.76$, $p<0.0001$. Fisher's LSD demonstrated that mean withdrawal thresholds were significantly higher compared to vehicle in 2.0-4.0 mg/kg CBD-Mono-VHS groups and drug combination of 0.1 mg/kg morphine and 1.0-4.0 mg/kg CBD-Mono-VHS groups ($ps \leq 0.0001$).

These results are consistent with those of example 23 and show this cisplatin administration protocol produces robust tactile allodynia in mice, a hallmark sign of chemotherapy-induced neuropathy. This tactile allodynia persisted for several days as evidenced by continued reduced paw withdrawal thresholds in vehicle-treated mice on drug efficacy screening day.

As in Example 23, mice receiving 2.5 mg/kg morphine displayed a robust attenuation of tactile allodynia. CBD-Mono-VHS produced a robust dose dependent attenuation of tactile allodynia equivalent to 2.5 mg/kg morphine at the 3.0 and 4.0 mg/kg doses. Further, this CBD-Mono-VHS dose response function shifted to the left by the addition of a sub-analgesic dose of morphine. This drug combination achieved a maximum effect at the 2.0 mg/kg CBD-Mono-VHS dose that was as efficacious as 2.5 mg/kg morphine alone. Collectively, these findings demonstrate that the 1) CBD-Mono-VHS alone produces robust analgesia equal to opioids against CIN and 2) these CBD-Mono-VHS effects can be achieved at lower doses when combined with sub-analgesic doses of an opioid agonist.

Example 25: Abuse Deterrent Effects of CBD and CBD-Val-HS in a Model of Addiction Method
Subjects C57BL/6 male mice (25-30 g) were group housed (n=5) in a polycarbonate tub with soft bedding in a temperature and humidity controlled vivarium. Mice were maintained under a 12:12 hour light/dark cycle with lights on at 06:00. Food and water were available ad libitum. Mice acclimated to the vivarium colony room one week prior to behavioral testing. All experimental procedures were approved on 18 May 2015 by the Institutional Animal Care Committee at the University of Mississippi (Protocol #15-022).

Apparatus

Five place preference chambers (Model MED-CPP-3013; Med Associates, St. Albans, Vt.) were used for these experiments. Each chamber has two stimulus-distinct conditioning chambers (Black versus white colored walls and wire or mesh metal rod flooring; 16.75×12.70 cm) separated by a third central start chamber (7.25×12.70 cm; colored grey with a smooth solid floor). Guillotine doors permitted confinement/access to individual chambers.

Procedure

The groups in this study formed a 2×6 factorial design that combined 2 levels of morphine and 6 levels of CBD and CBD-val-HS. Morphine Sulfate (Research Biomedical International; Natick, Mass.) was dissolved in 0.9% saline to yield a dosage of 2.5 mg/ml. Cannabidiol (>98% purity) solutions of 2.5, 5.0, 10.0, 20.0 mg/kg/mL and a single dose of CBD-val-HS 10.0 mg/kg/mL (ELI Laboratories; Oxford, Miss.) were dissolved in 5% ethanol, 5% Cremophor, and injectable water. Mice received dual IP administrations of test compounds.

Prior to behavioral testing, animals could acclimate to the testing room for at least 30 minutes. The CPP procedure consists of four phases: 1) a 15-min apparatus habituation trial, 2) a 15-min trial to establish baseline CPP scores, 3) six 45 min drug conditioning trials, and 4) a 15-min trial to establish post-conditioning CPP score. During the drug free habituation, baseline, and final preference trials animals were placed in the gray start chamber for a 5-minute adaption period. Following the adaption period the guillotine doors were lifted allowing access to the entire apparatus. The test apparatus was thoroughly cleaned with 70% ethanol solution after each trial.

CPP scores were determined by $$\frac{\text{Time in Black}}{\text{Time in Black} + \text{White}}$$

and led to the establishment of the S+ chamber for drug conditioning whereby S+ assigned to the non-preferred compartment. From these CPP scores, baseline and post-conditioning scores were calculated as $$\frac{\text{Time in } S+}{\text{Time in } S+ + S-}.$$

Preference scores was calculated by taking subtracting post-conditioning and baseline CPP scores with positive values reflecting reward and negative values reflecting aversion.

Statistical Analyses

Data were analyzed using SPSS software using two-way (between groups) ANOVA and one-way (between groups) ANOVA for simple effects analyses followed by planned comparisons (Fisher's LSD) for groups differences with significance at $p<0.05$.

Results

The effects of Cannabidiol and CBD-val-HS on Morphine conditioned place preference scores are summarized in FIG. 15. Preference scores were near zero in the control group (vehicle+saline) indicating there was little change in baseline and post-conditioning CPP scores. Morphine treated animals showed higher preference scores compared to the control group. Among the saline groups, CBD and CBD-val-HS did not show neither place preference nor aversion. Among the Morphine groups, CBD dose-dependently decreased preference scores that approached significance at 10 mg/kg CBD. Further, CBD-val-HS at 10.0 mg/kg fully and significantly abolished morphine place preference.

A two-way ANOVA revealed a significant main effect for Morphine $F(1.91)=24.57$, $p<0.001$ and a significant main effect for Cannabidiol $F(5.91)=2.843$, $p=0.021$. The Cannabidiol×Morphine interaction was not significant $F(5.91)=1.50$, $p=0.197$. To determine whether morphine possessed place preference, a one-way ANOVA of the Vehicle groups were conducted and revealed a significant effect for Morphine $F(1.15)=15.69$, $p<0.001$. To test whether CBD possessed rewarding or aversive properties, a one-way ANOVA among the Saline groups found no significant treatment effect $F(5.45)=1.311$, $p=0.276$. To determine whether CBD attenuated opioid reward, a one-way ANOVA on Morphine groups were performed and found a significant treatment effect $F(5.43)=2.984$, $p=0.021$.

Planned comparisons among the morphine groups found preference scores in the 10.0 mg/kg CBD approached significance ($p=0.051$) while CBD-val-HS had significantly lower preference scores than the CBD vehicle ($p=0.005$).

CONCLUSION

CBD-Mono-VHS significantly ($P=0.005$) blocked the addictive effects of morphine at 10 mg/kg while CBD at the same dose showed a tendency to block the addictive effects of morphine ($P=0.051$).

BRIEF DESCRIPTION OF THE FORMULATIONS OF THE INVENTION

The formulations of the present invention comprise a therapeutically effective amount of at least one biologically active cannabidiol analog composition of the formula wherein R1 is natural amino acid residue, and salts/derivatives thereof in an acceptable suppository base. The biologically active cannabidiol analogs consist essentially of biologically active cannabidiol analogs disclosed hereinabove.

The suppository formulation of this invention can be suppository formulations in which the suppository base is a hydrophilic base or a lipophilic base. The suppository formulation can advantageously comprise the suppository formulation base which is a hydrophilic base such as polyethylene glycol 1000.

The present invention also relates to a topical ophthalmic formulation biologically active cannabidiol analogs for reducing the intraocular pressure and/or inflammation in the treatment of glaucoma or eye inflammatory conditions, respectively. The formulation comprises a therapeutically effective amount of the present biologically active cannabidiol analogs and salts thereof in acceptable ophthalmic carrier.

A further embodiment of the invention relates to a Transmucosal Delivery Hot Melt Extrusion (HME) Patch formulation for the treatment of any disease condition responsive to CBD. The formulation comprises a therapeutically effective amount of at least one compound of the present biologically active cannabidiol analog compositions.

Suppository bases can be classified per their physical characteristics into two main categories and a third miscellaneous group: (a) fatty or oleaginous bases, (b) water-soluble or water-miscible bases, and (c) miscellaneous bases, generally combinations of lipophilic and hydrophilic substances.

Among the fatty or oleaginous materials used in suppository bases are cocoa butter and many hydrogenated fatty acids of vegetable oils, such as palm kernel oil and cottonseed oil. Also, fat-based compounds containing combinations of glycerin with the higher-molecular-weight fatty acids, such as palmitic and stearic acids, may be found in fatty bases. Such compounds, such as glyceryl monostearate and glyceryl monopalmitate, are examples of this type of agent. The bases in many commercial products employ varied combinations of these types of materials to achieve the desired hardness under conditions of shipment and storage and the desired quality of submitting to the temperature of the body to release their medicaments. Some bases are prepared with the fatty materials emulsified or with an emulsifying agent present to prompt emulsification when the suppository contacts the aqueous body fluids. These types of bases are arbitrarily placed in the third, or miscellaneous, group of bases.

Cocoa Butter, NF, is defined as the fat obtained from the roasted seed of *Theobroma cacao*. At room temperature, it is a yellowish-white solid having a faint, agreeable chocolate-like odor. Chemically, it is a triglyceride (combination of glycerin and one or different fatty acids) primarily of oleopalmitostearin and oleodistearin.

Other bases in this category include commercial products such as Fattibase (triglycerides from palm, palm kernel, and coconut oils with self-emulsifying glyceryl monostearate and polyoxyl stearate), the Wecobee bases (triglycerides derived from coconut oil) and Witepsol bases (triglycerides of saturated fatty acids C12-C18 with varied portions of the corresponding partial glycerides).

The main members of water-soluble and water-miscible suppository bases are glycerinated gelatin and polyethylene glycols. Glycerinated gelatin suppositories may be prepared by dissolving granular gelatin (20%) in glycerin (70%) and adding water or a solution or suspension of the medication (10%).

Polyethylene glycols are polymers of ethylene oxide and water prepared to various chain lengths, molecular weights, and physical states. They are available in several molecular weight ranges, the most commonly used being polyethylene glycol 300, 400, 600, 1,000, 1,500, 1,540, 3,350, 4,000, 6,000, and 8,000. The numeric designations refer to the average molecular weight of each of the polymers. Polyethylene glycols having average molecular weights of 300, 400, and 600 are clear, colorless liquids. Those having average molecular weights of greater than 1,000 are wax like white solids whose hardness increases with an increase in the molecular weight. Melting ranges for the polyethylene glycols follow:

| | |
|---|---|
| 300 | −15° C.-18° C. |
| 400 | 4° C.-8° C. |
| 600 | 20° C.-25° C. |
| 1000 | 37° C.-40° C. |
| 1450 | 43° C.-46° C. |
| 3350 | 54° C.-58° C. |
| 4600 | 57° C.-61° C. |
| 6000 | 56° C.-63° C. |
| 8000 | 60° C.-63° C. |

Various combinations of these polyethylene glycols may be combined by fusion, using two or more of the various types to achieve a suppository base of the desired consistency and characteristics.

In the miscellaneous group of suppository bases are mixtures of oleaginous and water-soluble or water-miscible materials. These materials may be chemical or physical mixtures. Some are preformed emulsions, generally of the water-in-oil type, or they may be capable of dispersing in aqueous fluids. One of these substances is polyoxyl 40 stearate, a surface-active agent that is employed in several commercial suppository bases. Polyoxyl 40 stearate is a mixture of the monostearate and distearate esters of mixed polyoxyethylene diols and the free glycols, the average polymer length being equivalent to about 40 oxyethylene units. The substance is a white to light tan waxy solid that is water soluble. Its melting point is generally 39° C. to 45° C. (102° F. to 113° F.). Other surface-active agents useful in the preparation of suppository bases also fall into this broad grouping. Mixtures of many fatty bases (including cocoa butter) with emulsifying agents capable of forming water-in-oil emulsions have been prepared. These bases hold water or aqueous solutions and are said to be hydrophilic.

The preferred suppository bases in the present invention are water soluble or water miscible bases.

The transmucosal device film or films (in the case of co-extrusion or layering) generally comprises at least one water-soluble, water-swellable or water-insoluble thermoplastic polymer. The thermoplastic polymer used to prepare the HME film may include, but is not limited to polyethylene oxide (PolyOx®), polyvinylpyrrolidone (Kollidon®), hydroxypropyl cellulose (Klucel®), ethyl cellulose, methylcellulose, alkylcelluloses, veegums clays, alginates, PVP, alginic acid, carboxymethylcellulose calcium, microcrystalline cellulose (e.g., Avicel™), polacrillin potassium (e.g., Amberlite™), sodium alginate, corn starch, potato starch, pregelatinized starch, modified starch, cellulosic agents, montmorrilonite clays (e.g., bentonite), gums, agar, locust bean gum, gum karaya, pecitin, tragacanth, and other matrix formers known to those skilled in the art.

This matrix may optionally contain a bio adhesive (such as a Carbopol, polycarbophil, chitosan or others known to those skilled in the art—to further enhance the bio-adhesivity of the cannabinoid itself) or a bio adhesive layer may be laminated onto the matrix film or patch containing the cannabinoid. In addition, an impermeable backing layer may be incorporated to insure unidirectional flow of the drug through the patient's mucosa. In some cases, a rate controlling film or membrane may also be laminated or sprayed onto the cannabinoid-containing matrix to further control the rate of release of the actives.

The transmucosal preparation will preferably contain a 'penetration enhancer' (which may also be referred to as an absorption enhancer or permeability enhancer). These penetration enhancers may include bile salts, such as sodium deoxycholate, sodium glycodeoxycholate, sodium taurocholate and sodium glycocholate, surfactants such as sodium lauryl sulfate, Polysorbate 80, laureth-9, benzalkonium chloride, cetylpyridinium chloride and polyoxyethylene monoalkyl ethers such as the BRIJ® and MYRJ® series. Additional penetration enhancers for inclusion in the embodiment include benzoic acids, such as sodium salicylate and methoxy salicylate, fatty acids, such as lauric acid, oleic acid, undecanoic acid and methyl oleate, fatty alcohols, such as octanol and nonanol, laurocapram, the polyols, propylene glycol and glycerin, cyclodextrins, the sulfoxides, such as dimethyl sulfoxide and dodecyl methyl sulfoxide, the terpenes, such as menthol, thymol and limonene, urea, chitosan and other natural and synthetic polymers.

The hot-melt extruded or hot-melt molded matrix may also comprise as bio adhesives such as water-soluble or water-swellable polymers derived from acrylic acid or a pharmaceutically acceptable salt thereof, such as the polyacrylic acid polymers, including carbomers, polycarbophils and/or water-soluble salts of a co-polymer of methyl vinyl ether and maleic acid or anhydride (Gantrez MS-955).

The transmucosal preparation can also comprise one or more pH-adjusting agents to improve stability and solubility. Also, the pH modifying agents can control cannabinoid release and enhance bio adhesion. A pH-adjusting agent can include, by way of example and without limitation, an organic acid or base, an alpha-hydroxy acid, or a beta-hydroxy acid. Suitable agents include tartaric acid, citric acid, fumaric acid, succinic acid and others known to those of ordinary skill in the art.

The transmucosal preparation can also comprise one or more cross-linking agents to reduce matrix erosion time, control release of the cannabinoid or enhance bio adhesion. A cross-linking agent can include, by way of example and without limitation, an organic acid, an alpha-hydroxy acid, or a beta-hemolytic-hydroxy acid. Suitable cross-linking agents include tartaric acid, citric acid, fumaric acid, succinic acid and others known to those of ordinary skill in the art.

The transmucosal preparation may also contain other components that modify the extrusion, molding or casting characteristics or physical properties of the matrix. Such other components are well known to those of ordinary skill in the pharmaceutical sciences and include, for example, polyethylene, xylitol, sucrose, surface-active agents, others known to those skilled in the art, and combinations thereof.

The transmucosal preparation of the present invention can also include super-disintegrants or absorbents. Examples of such are sodium starch glycolate (Explotab™, Primojel™) and croscarmellose sodium (Ac-Di-Sol®). Other suitable absorbents include cross-linked PVP (Polyplasdone™ XL 10), clays, alginates, corn starch, potato starch, pregelatinized starch, modified starch, cellulosic agents, montmorrilonite clays (bentonite), gums, agar, locust bean gum, gum karaya, pectin, tragacanth, and other disintegrants known to those of ordinary skill in the art.

The transmucosal preparation of the invention can include a chelating agent. Suitable chelating agents include EDTA, polycarboxylic acids, polyamines, derivatives thereof, and others known to those of ordinary skill in the art.

The transmucosal preparation of the invention can include a surfactant. Suitable surfactants include sucrose stearate, Vitamin E derivatives, sodium lauryl sulfate, dioctyl sodium sulfosuccinate, and others known to those of ordinary skill in the art.

The transmucosal preparation of the invention can include a preservative. Preservatives include compounds used to prevent the growth of microorganisms. Suitable preservatives include, by way of example and without limitation, benzalkonium chloride, propyl paraben, methyl paraben, benzyl alcohol, cetylpridinium chloride, chlorobutanol, sorbic acid, phenol, phenylethyl alcohol, phenylmercuric nitrate and thimerosal and others known to those of ordinary skill in the art.

As used herein, the term "flavorant", "flavor" or "fragrance" is intended to mean a compound used to impart a pleasant flavor and often odor to a pharmaceutical preparation, in addition to the natural flavorants, many synthetic flavorants are also used. Such compounds include, by way of example and without limitation, anise oil, cinnamon oil, cocoa, menthol, orange oil, peppermint oil and vanillin and others known to those of ordinary skill in the art. Flavors incorporated in the composition may be chosen from synthetic flavor oils and flavoring aromatics and/or natural oils, extract from plants, leaves, flowers, fruits and so forth and combinations thereof. These may include oil of wintergreen, clove oil, bay oil, anise oil, *eucalyptus*, thyme oil, cedar leaf oil, oil of nutmeg, oil of sage, oil of bitter almonds and *cassia* oil. Also, useful as flavors are vanilla, citrus oils, including lemon, orange, lime and grapefruit, and fruit essences, including grape, apple, pear, peach, strawberry, raspberry, cherry, plum, apricot, and so forth. Flavors that have been found to be particularly useful include commercially available orange, grape, cherry, and bubble gum flavors and mixtures thereof. The amount of flavoring may depend on several factors, including the organoleptic effect desired.

As used herein, the term "colorant" is intended to mean a compound used to impart color to solid pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide red. Other suitable colorants include titanium dioxide and natural coloring agents such as grape extract, beet red powder, carmine, turmeric, paprika, and others known to those of ordinary skill in the art.

The transmucosal preparation of the invention can include an antioxidant to prevent the deterioration of preparations by oxidation. These compounds include, by way of example and without limitation, ascorbic acid, ascorbyl palmitate, butylated hydroxyanisole (BHA), butylated hydroxytoluene (BHT), hypophosphorous acid, monothioglycerol, sodium ascorbate, sodium formaldehyde sulfoxylate and sodium metabisulfate and others known to those of ordinary skill in the art. Other suitable antioxidants include, for example, vitamin C, sodium bisulfite, vitamin E and its derivatives, propyl gallate, a sulfite derivative, and others known to those of ordinary skill in the art.

The transmucosal preparation of the invention may contain a release rate modifier. Suitable release rate modifiers include hydroxypropyl cellulose (HPC), poly (ethylene oxide) (PEO), hydroxypropyl methylcellulose (HPMC), ethyl cellulose, cellulosic polymers, acrylic polymers, fat, waxes, lipid, or a combination thereof, hi some embodiments, the release rate modifier is polycarbophil, carbomer or a polysaccharide.

The ingredients and chemicals used to produce the transmucosal preparation used in this invention are of acceptable quality, preferably pharmaceutically acceptable quality. The biologically active cannabidiol analogs-containing transmucosal preparation is homogenous and pharmaceutically acceptable.

The transmucosal preparation of the invention can include stabilizers to protect against hydrolysis. Such stabilizers may include cyclodextrins, chelating agents and surfactants.

The topical ophthalmic formulation can be solutions, emulsions, lipid nanoparticulate or matrix films. Other formulations known to one skilled in the art may also be used. The lipid nanoparticulate, emulsions and matrix films are the most preferred formulations.

Solutions: The solution formulations typically will require solubilizers in view of the low solubility of the cannabinoids. Examples of solubilizers that can be used in ophthalmic formulations include surfactants which form micellar solutions (since the active ingredient is entrapped in micelles) and complex forming agents or combinations thereof. Commonly used surfactants in ophthalmic formulations include polyoxyethylene sorbates (e.g. Tween® 20 and Tween® 80), polyoxyl hydrogenated castor oils (e.g. Cremphor® EL and Cremophor® RH 40), Tyloxapol®, polyoxyethyelene ethers (Brij® series) and alkoxylated fatty acid esters (Myrj® series), sorbitan esters (Span® series) and others know to a person skilled in the art. Cyclodextrins, such as hydroxypropyl betacyclodextrin and randomlymethylated beta cyclodextrins, are commonly used to enhance solubility through inclusion complex formation. The solubilizers may be used alone or in combination.

Emulsions: An emulsion is a system consisting of two immiscible liquid phases (oil and water), one of which is dispersed throughout the other as fine droplets, the system being stabilized by a third component, the emulsifying agent. Emulsions are inherently unstable, and emulsifiers are essential for both their initial formation and long-term stability. Emulsions may be oil in water (oil phase dispersed in the aqueous phase) or water in oil (water phase dispersed in the oil phase) emulsions. A variety of other systems such as oil in water in oil emulsions and water in oil in water emulsions are also known in the art. The oil phase may consist of oils such as soyabean oil, castor oil, sesame oil and olive oil. Several emulsion stabilizers or emulsifying agents are known in the art and include surfactants and phospholipids. Examples of surfactant emulsifiers include polyoxyethylene sorbates (e.g. Tween® 20 and Tween® 80), polyoxyl hydrogenated castor oils (e.g. Cremphor® EL and Cremophor® RH 40), Tyloxapol®, polyoxyethyelene ethers (Brij® series) and alkoxylated fatty acid esters (Myrj® series), sorbitan esters (Span® series) and others know to a person skilled in the art. Examples of phospholipids that may be used as emulsion stabilizers include phospholipids (e.g. phosphatidylcholine, phosphatidylinositol, phosphatidylglycerol).

Lipid nanoparticles: Colloidal dispersions of solid lipid nanoparticles (SLNs) or nanostructured lipid carriers (NLCs) containing the therapeutic agent may also be used. In these systems, the drug is loaded in the lipid phase, which is then dispersed in the aqueous phase. In the design of SLNs, only lipids that are solid at room temperature are used whereas with NLCs a combination of solid (e.g. Compritol®, Precirol®) and liquid lipids (e.g. Miglyol®) are used. Additionally, stabilizers such as surfactants and other components such as glycerine and propylene glycol may also be used alone and in combination thereof.

Matrix films: Matrix films prepared using melt-extrusion or melt-cast technology can also be used. The films comprise a thermoplastic polymer as the carrier of the active ingredient. The thermoplastic polymer used may include, but is not limited to polytheylene oxide (PolyOx®), polyvinylpyrrolidone (Kollidon®), hydroxypropyl cellulose (Klucel®), ethyl cellulose, methylcellulose, alkylcelluloses, veegums clays, alginates, PVP, alginic acid, carboxymethylcellulose calcium, microcrystalline cellulose (e.g., Avicel™), polacrillin potassium (e.g., Amberlite™), sodium alginate, corn starch, potato starch, pregelatinized starch, modified starch, cellulosic agents, montmorrilonite clays (e.g., bentonite), gums, agar, locust bean gum, gum karaya, pecitin, tragacanth, and other matrix formers known to those skilled in the art. The matrix film may also comprise of bioadhesives such as water-soluble or water-swellable polymers derived from acrylic acid or a pharmaceutically acceptable salt thereof, such as the polyacrylic acid polymers, including carbomers, polycarbophils and/or water-soluble salts of a co-polymer of methyl vinyl ether and maleic acid or anhydride (Gantrez MS-955).

The topical ophthalmic compositions may include additional or alternative polymeric ingredients and/or viscosity agents to increase stability and/or retention on the ocular surface. Examples include carboxymethylcellulose, hydroxypropyl methyl cellulose, hydroxyethyl cellulose, carboxyvinyl polymer, xanthan gum, hyaluronic acid, any combinations thereof or the like.

The topical ophthalmic compositions may include a preservative. Potential preservatives include quaternary ammonium compounds such as benzalkonium chloride, hydrogen peroxide and other ophthalmic preservatives/preservative systems known in the art.

Other additives such as buffers and tonicity adjusting agents may also be included in the topical ophthalmic formulations. Examples of buffering agents include citrate, borate and acetate buffers. Tonicity adjusting agents may include for example sodium chloride and potassium chloride. Additionally, stabilizers (e.g. antioxidants and chelating agents) and penetration enhancers e.g. benzalkonium chloride, saponins, fatty acids, polyoxyethylene fatty ethers, alkyl esters of fatty acids, pyrrolidones, polyvinylpyrrolidone, pyruvic acids, pyroglutamic acids and their mixtures, among others, may also be included.

The above description is only representative of illustrative embodiments and examples. For the convenience of the reader, the above description has focused on a limited number of representative examples of all possible embodiments, examples that teach the principles of the invention. The description has not attempted to exhaustively enumerate all possible variations or even combinations of those variations described. That alternate embodiments may not have been presented for a specific portion of the invention, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the invention. Accordingly, the invention is not intended to be limited to less than the scope set forth in the following claims and equivalents.

REFERENCES

Alexander A, Smith, P F Rosengren, R J. Cannabinoids in the treatment of cancer. Cancer Letters 2009; 285:6-12.

Amptoulach S, Tsavaris N. Neurotoxicity caused by the treatment with platinum analogues. Chemotherapy Research and Practice. 2011; Article ID 843019.

Basbaum A I, Fields H L. Endogenous pain control systems: brainstem spinal pathways and endorphin circuitry. Annual Review of Neuroscience. 1984; 7: 309-338.

Chiou L C, Hu S S, Ho Y. Targeting the cannabinoid system for pain relief?Act Anaesthesiologica Taiwanica. 2013; 51:161-170.

Cox M L, Haller V L, Welch S P. Synergy between Δ9-tetrahydrocannabinol and morphine in the arthritic rat. European Journal of Pharmacology. 2007; 567: 125-130.

Guindon J, Lai Y, Takacs S M, Bradshaw H B, Hohmann A G. Alterations in endocannabionid tone following chemotherapy-induced peripheral neuropathy: effects of endocannabinoid deactivation inhibitors targeting fatty-acid amide hydrolase and monoacylglycerol lipase in comparison to reference analgesics following cisplatin treatment. Pharmacological Research. 2012; 67, 94-109.

Hall W, Christie M, Currow D. Cannabinoids and cancer: causation, remediation, and palliation. The Lancet. 2005; 6:35-42.

Khasabova I A, Khasabov S, Paz J, Rose C, Simone D A. Cannabinoid type-1 receptor reduces pain and neurotoxicity produced by chemotherapy. Neurobiology of Disease. 2012; 32, 7091-7101.

Kim, J H, Dougherty P M, Abdi S. Basic science and clinical management of painful and non-painful chemotherapy-related neuropathy. Gynecologic Oncology. 2015; 136: 453-459.

Mansour A, Khachaturian H, Lewis M E, Akil H, Watson S J. Anatomy of CNS opioid receptors. Trends in Neuroscience. 1988; 11: 308-314.

Miltenburg N C, Booger W. Chemotherapy-induced neuropathy: a comprehensive survey. Cancer Treatment Reviews. 2014; 40:872-882.

Neelakantan H, Tallarida R J, Reishcenbach Z W, Tuma R F, Ward S J, Walker E A. Distinct interactions of cannabidiol and morphine in three nociceptive behavioral models in mice. Behavioural Pharmacology. 2014; 26:304-314.

Paice J A. Chronic treatment-related pain in cancer survivors. Pain. 2010; 152:84-89.

Park H J, Stokes J A, Pirie E, Skahen J, Shtaerman Y, Yaksh T L. Persistent hyperalgesia in the cisplatin-treated mouse as defined by threshold measures, the conditioned place preference paradigm, and the changes in dorsal root ganglia activated transcription factor 3: the effects of gabapentin, ketorolac, and entanercept. Anesthesia and Analgesia. 2012; 116:224-231.

Pisanti S, Picardi P, D'Alessandro A, Laezza C, Bifulco M. The endocannabinoid signaling system in cancer. Trends in Pharmacological Sciences. 2013; 34, 273-282.

Toth C., Au S. A prospective identification of neuropathic pain in specific chronic polyneuropathy syndromes and response to pharmacological therapy. Pain. 2008; 138: 657-666.

Vera G, Cabezos P A, Martin M I, Abalo R. Characterization of cannabinoid-induced relief of neuropathic pain in a rat model of cisplatin-induced neuropathy. Pharmacology, Biochemistry and Behavior. 2013; 105, 205-212.

Wilson-Poe A R, Pocius E, Herschbach M, Morgan M M. The periaqueductal gray contributes to bi-directional enhancement of antinociception between morphine and cannabinoids. Pharmacology, Biochemistry and Behavior. 2013; 103: 444-449.

Wolf S., Barton D., Kottschade L., Grothey A., Lopriniz C. Chemotherapy-induced peripheral neuropathy: prevention and treatment strategies. European Journal of Cancer. 2008; 44:1507-1515.

What we claim is:

1. A biologically active cannabidiol analog of the formula I

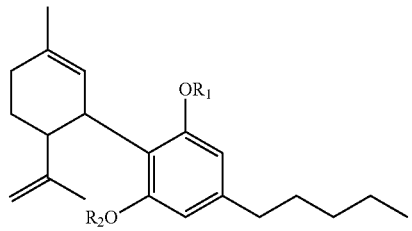

wherein one of $R_1$ or $R_2$ is H and the other is an amino acid ester amide or both $R_1$ and $R_2$ are an amino acid ester amide; or one of $R_1$ or $R_2$ is the amino acid ester amide and the other $R_1$ or $R_2$ is the ester residue of a dicarboxylic acid or dicarboxylic acid halide; wherein the amino acid ester amide comprises an amino acid linked to one or both of the hydroxyl groups of cannabidiol through an ester linkage and a dicarboxylic acid or dicarboxylic acid halide to the amino group of the amino acid in an amide linkage, wherein the amino acid is one of Alanine, Arginine, Asparagine, Aspartic Acid, Cysteine, Glutamine, Glutamic Acid, Glycine, Histidine, Isoleucine, Leucine, Lysine, Methionine, Phenylalanine, Proline, Serine, Threonine, Tryptophan, Tyrosine and Valine, and a pharmaceutically acceptable salt thereof.

2. The biologically active cannabidiol analog of claim 1, wherein the dicarboxylic acid is an organic compound containing two carboxyl functional groups having the formula $HO_2C-R-CO_2H$, where R is a straight chain or branched aliphatic or aromatic lower alkyl.

3. The analog of claim 1, wherein the compound is CBD-Di-Alaninate-Di-Hemisuccinate, CBD-Divalinate-Di-Hemisuccinate, CBD-Mono-Valinate-Mono-Hemisuccinate, or CBD-monovalinate-dihemisuccinate.

4. A biologically active cannabidiol analog of claim 1 which is CBD-Divalinate-Di-Hemisuccinate, having the formula

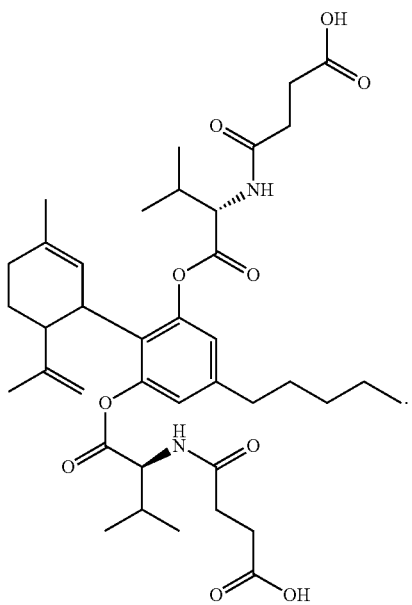 [SMILES: C=C(C)C1CCC(C)=CC1c1c(OC(=O)[C@@H](NC(=O)CCC(=O)O)C(C)C)cc(CCCCC)cc1OC(=O)[C@@H](NC(=O)CCC(=O)O)C(C)C]

5. A biologically active cannabidiol analog of claim 1 which is CBD-Monovalinate-Di-Hemisuccinate, having the formula

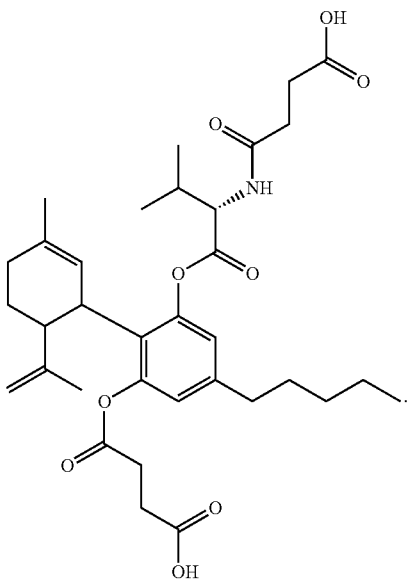 [SMILES: C=C(C)C1CCC(C)=CC1c1c(OC(=O)CCC(=O)O)cc(CCCCC)cc1OC(=O)[C@@H](NC(=O)CCC(=O)O)C(C)C]

6. A biologically active cannabidiol analog of claim 1 which is CBD-Monovalinate-Mono-Hemisuccinate, having the formula

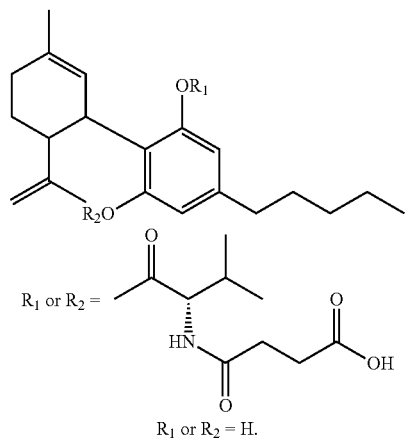

7. A pharmaceutical composition comprising the biologically active cannabidiol analog of claim 1 in a pharmaceutically acceptable carrier.

8. A pharmaceutical composition comprising the biologically active cannabidiol analog of claim 3 in a pharmaceutically acceptable carrier.

9. The biologically active cannabidiol analog of claim 1, wherein the dicarboxylic acid is malonic acid, malic acid, glutaric acid, succinic acid, and phthalic acid.

10. A pharmaceutical composition comprising the biologically active cannabidiol analog of claim 6 in a pharmaceutically acceptable carrier.

11. A biologically active cannabidiol analog of the formula I

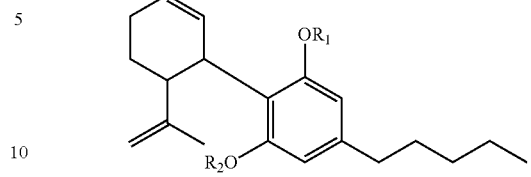

wherein one of $R_1$ or $R_2$ is H and the other is an amino acid ester amide, wherein the amino acid ester amide comprises an amino acid linked to one of the hydroxyl groups of cannabidiol through an ester linkage and a dicarboxylic acid or dicarboxylic acid halide to the amino group of the amino acid in an amide linkage wherein the amino acid is one of Alanine, Arginine, Asparagine, Aspartic Acid, Cysteine, Glutamine, Glutamic Acid, Glycine, Histidine, Isoleucine, Leucine, Lysine, Methionine, Phenylalanine, Proline, Serine, Threonine, Tryptophan, Tyrosine and Valine, and a pharmaceutically acceptable salt thereof.

12. The biologically active cannabidiol analogs of claim 11, wherein the dicarboxylic acid is an organic compound containing two carboxyl functional groups having the formula $HO_2C$—R—$CO_2H$, where R is a straight chain or branched aliphatic or aromatic lower alkyl.

13. The compound of claim 11, wherein the compound is CBD-Mono-Valinate-Mono-Hemisuccinate.

14. The compound of claim 11, which is CBD-Divalinate-Di-Hemisuccinate, having the formula

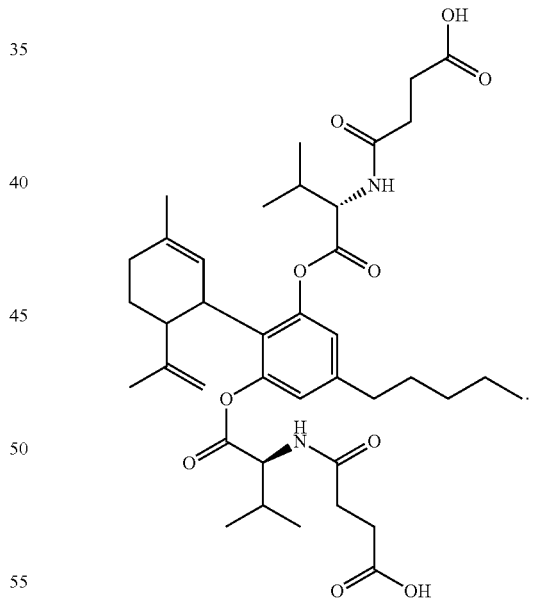

15. A pharmaceutical composition comprising the biologically active cannabidiol analog of claim 11 in a pharmaceutically acceptable carrier.

16. The biologically active cannabidiol analog of claim 11, wherein the dicarboxylic acid is malonic acid, malic acid, glutaric acid, succinic acid, and phthalic acid.

17. A pharmaceutical composition comprising the biologically active cannabidiol analog of claim 3 in a pharmaceutically acceptable carrier.

* * * * *